(12) United States Patent
Lee et al.

(10) Patent No.: US 11,738,144 B2
(45) Date of Patent: Aug. 29, 2023

(54) TECHNIQUES ENABLING ADAPTATION OF PARAMETERS IN AID SYSTEMS BY USER INPUT

(71) Applicant: INSULET CORPORATION, Acton, MA (US)

(72) Inventors: Joon Bok Lee, Acton, MA (US); Bonnie Dumais, Hudson, NH (US); Jason O'Connor, Acton, MA (US); Yibin Zheng, Hartland, WI (US)

(73) Assignee: INSULET CORPORATION, Acton, MA (US)

( * ) Notice: Subject to any disclaimer, the term of this patent is extended or adjusted under 35 U.S.C. 154(b) by 0 days.

(21) Appl. No.: 17/935,483

(22) Filed: Sep. 26, 2022

(65) Prior Publication Data

US 2023/0095302 A1    Mar. 30, 2023

Related U.S. Application Data

(60) Provisional application No. 63/248,844, filed on Sep. 27, 2021.

(51) Int. Cl.
*A61M 5/172* (2006.01)
*A61M 5/142* (2006.01)

(52) U.S. Cl.
CPC ...... *A61M 5/1723* (2013.01); *A61M 5/14244* (2013.01); *A61M 2230/201* (2013.01)

(58) Field of Classification Search
CPC ............ A61M 5/1723; A61M 5/14244; A61M 5/142; A61M 5/14248; A61B 5/14532; A61B 5/4839; G16H 20/17; A61K 38/28
See application file for complete search history.

(56) References Cited

U.S. PATENT DOCUMENTS 303,013 A    8/1884   Horton
2,797,149 A  6/1957   Skeggs
(Continued)

FOREIGN PATENT DOCUMENTS

AU   2015200834 A1   3/2015
AU   2015301146 A1   3/2017
(Continued)

OTHER PUBLICATIONS

US 5,954,699 A, 09/1999, Jost et al. (withdrawn)
(Continued)

*Primary Examiner* — Manuel A Mendez
(74) *Attorney, Agent, or Firm* — Goodwin Procter LLP

(57) ABSTRACT

Disclosed are techniques and devices that are operable to receive one or a number of generalized parameters of an automated insulin delivery algorithm. An input of at least one generalized parameter corresponding to a user may be used to set one or more of the number of specific parameters of the automated insulin delivery algorithm based on the inputted at least one generalized parameter. Physiological condition data related to the user may be collected. The automated insulin delivery algorithm may determine a dosage of insulin to be delivered based on the collected physiological condition. Signals may be output to cause a liquid drug to be delivered to the user based on an output of the automated insulin delivery algorithm related to the determined dosage of insulin.

20 Claims, 10 Drawing Sheets

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Grothall |
| 6,050,978 A | 4/2000 | Or et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |

(56) References Cited

U.S. PATENT DOCUMENTS

| | | |
|---|---|---|
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | L. Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |

(56) References Cited

U.S. PATENT DOCUMENTS

| | | |
|---|---|---|
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |

(56) References Cited

U.S. PATENT DOCUMENTS

| | | |
|---|---|---|
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Ison et al. |
| 2013/0030358 A1 | 1/2013 | Yodat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0200426 A1 | 1/2014 | Taub et al. |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0189625 A1 | 7/2017 | Cirillo et al. |
| 2017/0203039 A1 * | 7/2017 | Desborough ..... A61M 5/14244 |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0143031 A1 * | 5/2019 | Admani ............... A61M 5/168 |
| | | 604/65 |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | | |
|---|---|---|---|
| CA | 2859561 A1 * | 6/2013 | ........... A61B 5/0022 |
| CN | 1297140 A | 5/2001 | |
| DE | 19756872 A1 | 7/1999 | |
| EP | 0341049 A2 | 11/1989 | |
| EP | 0496305 A2 | 7/1992 | |
| EP | 0549341 A1 | 6/1993 | |
| EP | 1491144 A1 | 12/2004 | |
| EP | 0801578 B1 | 7/2006 | |
| EP | 2139382 A1 | 1/2010 | |
| EP | 2397181 A1 | 12/2011 | |
| EP | 2666520 A1 | 11/2013 | |
| EP | 2695573 A2 | 2/2014 | |
| EP | 2830499 A1 | 2/2015 | |
| EP | 2943149 A1 | 11/2015 | |
| EP | 3177344 A1 | 6/2017 | |
| EP | 3314548 A1 | 5/2018 | |
| EP | 1571582 B1 | 4/2019 | |
| EP | 2897071 B1 | 5/2019 | |
| EP | 3607985 A1 | 2/2020 | |
| GB | 2443261 A | 4/2008 | |
| JP | 51125993 A | 11/1976 | |
| JP | 02131777 A | 5/1990 | |
| JP | 2004283378 A | 10/2007 | |
| JP | 2017525451 A | 9/2017 | |
| JP | 2018153569 A | 10/2018 | |

(56) References Cited

FOREIGN PATENT DOCUMENTS

| | | | |
|---|---|---|---|
| JP | 2019525276 A | | 9/2019 |
| TR | 201820021 | * | 4/2019 |
| TW | 200740148 A | | 10/2007 |
| TW | M452390 U | | 5/2013 |
| WO | 9800193 A1 | | 1/1998 |
| WO | 9956803 A1 | | 11/1999 |
| WO | 0030705 A1 | | 6/2000 |
| WO | 200032258 A1 | | 6/2000 |
| WO | 0172354 A2 | | 10/2001 |
| WO | 2002015954 A1 | | 2/2002 |
| WO | 2002043866 A2 | | 6/2002 |
| WO | 2002082990 A1 | | 10/2002 |
| WO | 2003016882 A1 | | 2/2003 |
| WO | 2003039362 A1 | | 5/2003 |
| WO | 2003045233 A1 | | 6/2003 |
| WO | 2004043250 A1 | | 5/2004 |
| WO | 2005110601 A1 | | 5/2004 |
| WO | 2004092715 A1 | | 10/2004 |
| WO | 2005051170 A2 | | 6/2005 |
| WO | 2005082436 A1 | | 9/2005 |
| WO | 2005113036 A1 | | 12/2005 |
| WO | 2006053007 A2 | | 5/2006 |
| WO | 2007064835 A2 | | 6/2007 |
| WO | 2007078937 A1 | | 7/2007 |
| WO | 2008024810 A2 | | 2/2008 |
| WO | 2008029403 A1 | | 3/2008 |
| WO | 2008133702 A1 | | 11/2008 |
| WO | 2009045462 A1 | | 4/2009 |
| WO | 2009049252 A1 | | 4/2009 |
| WO | 2009066287 A3 | | 5/2009 |
| WO | 2009066288 A1 | | 5/2009 |
| WO | 2009098648 A2 | | 8/2009 |
| WO | 2009134380 A2 | | 11/2009 |
| WO | 2010053702 A1 | | 5/2010 |
| WO | 2010132077 A1 | | 11/2010 |
| WO | 2010138848 A1 | | 12/2010 |
| WO | 2010147659 A2 | | 12/2010 |
| WO | 2011095483 A1 | | 8/2011 |
| WO | 2012045667 A2 | | 4/2012 |
| WO | 2012108959 A1 | | 8/2012 |
| WO | 2012134588 A1 | | 10/2012 |
| WO | 2012177353 A1 | | 12/2012 |
| WO | 2012178134 A2 | | 12/2012 |
| WO | 2013078200 A1 | | 5/2013 |
| WO | 2013134486 A2 | | 9/2013 |
| WO | 20130149186 A1 | | 10/2013 |
| WO | 2013177565 A1 | | 11/2013 |
| WO | 2013182321 A1 | | 12/2013 |
| WO | 2014109898 A1 | | 7/2014 |
| WO | 2014110538 A1 | | 7/2014 |
| WO | 2014194183 A2 | | 12/2014 |
| WO | 2015056259 A1 | | 4/2015 |
| WO | 2015061493 A1 | | 4/2015 |
| WO | 2015073211 A1 | | 5/2015 |
| WO | 2015081337 A2 | | 6/2015 |
| WO | 2015187366 A1 | | 12/2015 |
| WO | 2016004088 A1 | | 1/2016 |
| WO | 2016022650 A1 | | 2/2016 |
| WO | 2016041873 A1 | | 3/2016 |
| WO | 2016089702 A1 | | 6/2016 |
| WO | 2016141082 A1 | | 9/2016 |
| WO | 2016161254 A1 | | 10/2016 |
| WO | 2017004278 A1 | | 1/2017 |
| WO | 2017091624 A1 | | 6/2017 |
| WO | 2017105600 A1 | | 6/2017 |
| WO | 2017184988 A1 | | 10/2017 |
| WO | 2017205816 A1 | | 11/2017 |
| WO | 2018009614 A1 | | 1/2018 |
| WO | 2018067748 A1 | | 4/2018 |
| WO | 2018120104 A1 | | 7/2018 |
| WO | 2018136799 A1 | | 7/2018 |
| WO | 2018204568 A1 | | 11/2018 |
| WO | 2019077482 A1 | | 4/2019 |
| WO | 2019094440 A1 | | 5/2019 |
| WO | 2019213493 A1 | | 11/2019 |
| WO | 2019246381 A1 | | 12/2019 |
| WO | 2020081393 A1 | | 4/2020 |
| WO | 2021011738 A1 | | 1/2021 |

OTHER PUBLICATIONS

Translation of TR201820021 (Year: 2019).*
International Search Report and Written Opinion for the International Patent Application No. PCT/US2020/052125, dated Aug. 12, 2020, 15 pages.
International Search Report and Written Opinion for the International Patent Application No. PCT/US2020/050332, dated Sep. 12, 2020, 12 pages.
European Patent Office, "Notification of Transmittal of the ISR and the Written Opinion of the International Searching Authority, or the Declaration," in PCT Application No. PCT/GB2015/050248, dated Jun. 23, 2015, 12 pages.
International Search Report and Written Opinion for the International Patent Application No. PCT/US2021/012246, dated Apr. 13, 2021, 15 pages.
International Search Report and Written Opinion for the International Patent Application No. PCT/US2021/013639, dated Apr. 28, 2021, 14 pages.
International Search Report and Written Opinion for the International Patent Application No. PCT/US2020/063326, dated May 3, 2021, 17 pages.
European Search Report for the European Patent Application No. 21168591, dated Oct. 13, 2021, 4 pages.
International Search Report and Written Opinion for the International Patent Application No. PCT/US2021/041954, dated Oct. 25, 2021, 13 pages.
International Search Report and Written Opinion for the International Patent Application No. PCT/US2021/022694, dated Jun. 25, 2021, 13 pages.
International Search Report and Written Opinion for the International Patent Application No. PCT/US2021/017664, dated May 26, 2021, 16 pages.
International Search Report and Written Opinion for the International Patent Application No. PCT/US2022/012896, dated Apr. 22, 2022, 15 pages.
International Search Report and Written Opinion for the International Patent Application No. PCT/US2022/013470, dated May 6, 2022, 14 pages.
International Search Report and Written Opinion for the International Patent Application No. PCT/US2022/013473, dated May 6, 2022, 13 pages.
International Search Report and Written Opinion for the International Patent Application No. PCT/US2022/019079, dated Jun. 2, 2022, 14 pages.
International Search Report and Written Opinion for the International Patent Application No. PCT/US2022/018453, dated Jun. 2, 2022, 13 pages.
International Search Report and Written Opinion for the International Patent Application No. PCT/US22/018700, dated Jun. 7, 2022, 13 pages.
International Search Report and Written Opinion for the International Patent Application No. PCT/US22/019080, dated Jun. 7, 2022, 14 pages.
International Search Report and Written Opinion for the International Patent Application No. PCT/US22/019664, dated Jun. 7, 2022, 14 pages.
International Search Report and Written Opinion for International Patent Application No. PCT/US2021/051027, dated Jan. 7, 2022, 16 pages.
International Search Report and Written Opinion for International Patent Application No. PCT/US2021/052372, dated Jan. 26, 2022, 15 pages.
International Search Report and Written Opinion for the International Patent Application No. PCT/US2021/046607, dated Jan. 31, 2022, 20 pages.

(56) References Cited

OTHER PUBLICATIONS

International Search Report and Written Opinion for the International Patent Application No. PCT/US2021/055745, dated Feb. 14, 2022, 13 pages.
International Search Report and Written Opinion for the International Patent Application No. PCT/US21/060618, dated Mar. 21, 2022, 15 pages.
Herrero Pau et al: "Enhancing automatic closed-loop glucose control in type 1 diabetes with an adaptive meal bolus calculator-in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprintsand permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
International Search Report and Written Opinion for the International Patent Application No. PCT/US2021/052855, dated Dec. 22, 2021, 11 pages.
International Search Report and Written Opinion for the International Patent Application No. PCT/US2021/047771, dated Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Leet. Notes Comp. Sci vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Sep. 7, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, dated Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, dated May 16, 2017, 12 pages.
International Search Report and Written Opinion for the International Patent Application No. PCT/US2018/018901, dated Aug. 6, 2018,12 pages.
International Search Report and Written Opinion for International Patent Application No. PCT/US2018/052467, dated Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on iOS 11", GoToTags, Sep. 11, 2017, web <https://gototags.com/blog/read-nfc-tags-with-an-iphone-app-on-ios-11/>. (Year:2017).
International Search Report and Written Opinion for International Patent Application No. PCT/US2016/063350, dated Mar. 27, 2017, 9 pages.
Extended Search Report dated Aug. 13, 2018, issued in European Patent Application No. 16753053.4, 9 pages.
International Search Report and Written Opinion for International Patent Application No. PCT/US16/18452, dated Apr. 29, 2015, 9 pages.
International Preliminary Report on Patentability dated Aug. 31, 2017, issued in PCT Patent Application No. PCT/US2016/018452, 7 pages.
International Search Report and Written Opinion for International Patent Application No. PCT/US2019/055862, dated Mar. 11, 2020.
International Search Report and Written Opinion for Application No. PCT/US2019/030562, dated Sep. 25, 2019, 19 pages.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.

(56) References Cited

OTHER PUBLICATIONS

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, dated Jun. 2, 2021, 15 pages.

Farkas et al. "Single-Versus Triple-Lumen Central Catheter-Related Sepsis: A Prospective Randomized Study in a Critically III Population" The American Journal of Medicine, Sep. 1992, vol. 93, p. 277-282.

Davidson, Paul C., et al., A computer-directed intravenous insulin system shown to be safe, simple,and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination Of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically III Patients, The New England Journal of Medicine, vol. 345, No. 19, Nov. 8, 2001, pp. 1359-1367.

Schlegel et al., "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 dated Jul. 16, 2010 (OPTIS. 247VPC).

International Search Report and Written Opinion in PCT/US2008/079641 (Optis.203VPC) dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 323-627, Feb. 1, 1998.

Billman et al.,"Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved on Dec. 29, 2010 from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.

International Preliminary Report on Patentability for the International Patent Application No. PCT/US2019/053603, dated Apr. 8, 2021, 9 pages.

International Search Report and Written Opinion for the International Patent Application No. PCT/US2019/053603, dated Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, dated May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, dated May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, dated May 27, 2021, 16 pages.

International Search Report and Written Opinion for the International Patent Application No. PCT/US2020/065226, dated May 31, 2021, 18 pages.

International Search Report and Written Opinion for the International Patent Application No. PCT/US2021/017659, dated May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

\* cited by examiner

TECHNIQUES ENABLING ADAPTATION OF PARAMETERS IN AID SYSTEMS BY USER INPUT

RELATED APPLICATIONS

This application claims the benefit of U.S. Provisional Patent Application No. 63/248,844, filed Sep. 27, 2021, the contents of which are incorporated herein by reference in their entirety.

BACKGROUND

Wearable drug delivery devices operate using a number of parameters that may be based on a user's history with wearable drug delivery devices. However, when a person is recently diagnosed with diabetes, the user usually does not yet have a user history with a drug delivery device. As a result, the user or the user's healthcare provider may have to perform what can be the daunting and tedious task of inputting the number of parameters into an automated insulin delivery (AID) algorithm that controls the delivery of insulin from the wearable drug delivery device.

AID algorithms for patients with Type 1 and Type 2 diabetes are evolving to simplify the onboarding experience of new users (e.g., no need to enter clinical parameters, such as basal profile, insulin-to-carbohydrate (IC) ratio, and/or correction factor (CF)). This development correspondingly causes an increasing "obfuscation" in the ways new users can impact, which may be adversely, the performance of these systems. The complexity of the calculations performed by the AID algorithms using the clinical parameters may make new users as well as some healthcare providers weary of adjusting the parameter settings, as such, the adjusted parameter settings may not provide an optimal outcome for the user.

In addition, as AID systems for T1DM management approach the capability to provide fully automated control of a user's diabetes treatment plan, there is still a desire by users or their healthcare providers to be able to optionally alter the automated calculation of system settings. For instance, an AID system may assume initial values for the user's clinical input parameters such as the basal profile, the IC ratio and the CF based on the user's insulin history, but the users may desire to modify such input parameters for their own reasons.

It would be beneficial to have techniques and devices that enable generalized adjustment of the parameter settings of an AID algorithm without the inadvertent obfuscation of the functions of the AID algorithm.

BRIEF SUMMARY

In one aspect, a controller is presented. The controller includes a processor, an input/output device, and a memory storing instructions. The instructions when executed by the processor may configure the processor to present, on the input/output device, a graphical user interface offering an input field for a sole generalized parameter of an automated insulin delivery algorithm. An input of the sole generalized parameter may be received via the input/output device. In response to receiving the input of the sole generalized parameter, a specific parameter of the automated insulin delivery algorithm may be set based on the inputted sole generalized parameter. The automated insulin delivery algorithm with the set specific parameter may determine a dosage of insulin to be delivered to the user. The determined dosage of insulin may be caused to be delivered to the user.

In a further aspect, a method is provided. The method includes presenting, on an input/output device of a user device, a graphical user interface offering an input field for a sole generalized parameter of an automated insulin delivery algorithm. An input of the sole generalized parameter may be received. In response to receiving the input of the sole generalized parameter, a specific parameter of the automated insulin delivery algorithm may be set based on the inputted sole generalized parameter. A dosage of insulin to be delivered to a user may be determined by the automated insulin delivery algorithm using the set specific parameter. The determined dosage of insulin may be caused to be delivered to the user.

In another aspect, a system is provided that includes a non-transitory computer-readable storage medium. The computer-readable storage medium may include instructions that when executed by at least one processor, cause the at least one processor to present, on an input/output device, a graphical user interface offering an input field for a generalized parameter of the automated insulin delivery algorithm. An input of only one generalized parameter may be received via the input/output device. In response to receiving the input of the only one generalized parameter, a specific parameter of the automated insulin delivery algorithm may be set based on the inputted generalized parameter. The automated insulin delivery algorithm using the set specific parameter may determine a dosage of insulin to be delivered to the user. The determined dosage of insulin may be caused to be delivered to the user.

BRIEF DESCRIPTION OF THE DRAWINGS

In the drawings, like reference characters generally refer to the same parts throughout the different views. In the following description, various embodiments of the present disclosure are described with reference to the following drawings, in which.

DETAILED DESCRIPTION

The disclosed techniques and devices provide the user with input devices that allow for the input of generalized AID algorithm parameters that are interpretable by the AID algorithm for use in the complex calculations that control a wearable drug delivery device according to the user's diabetes treatment plan.

Figure 1A:
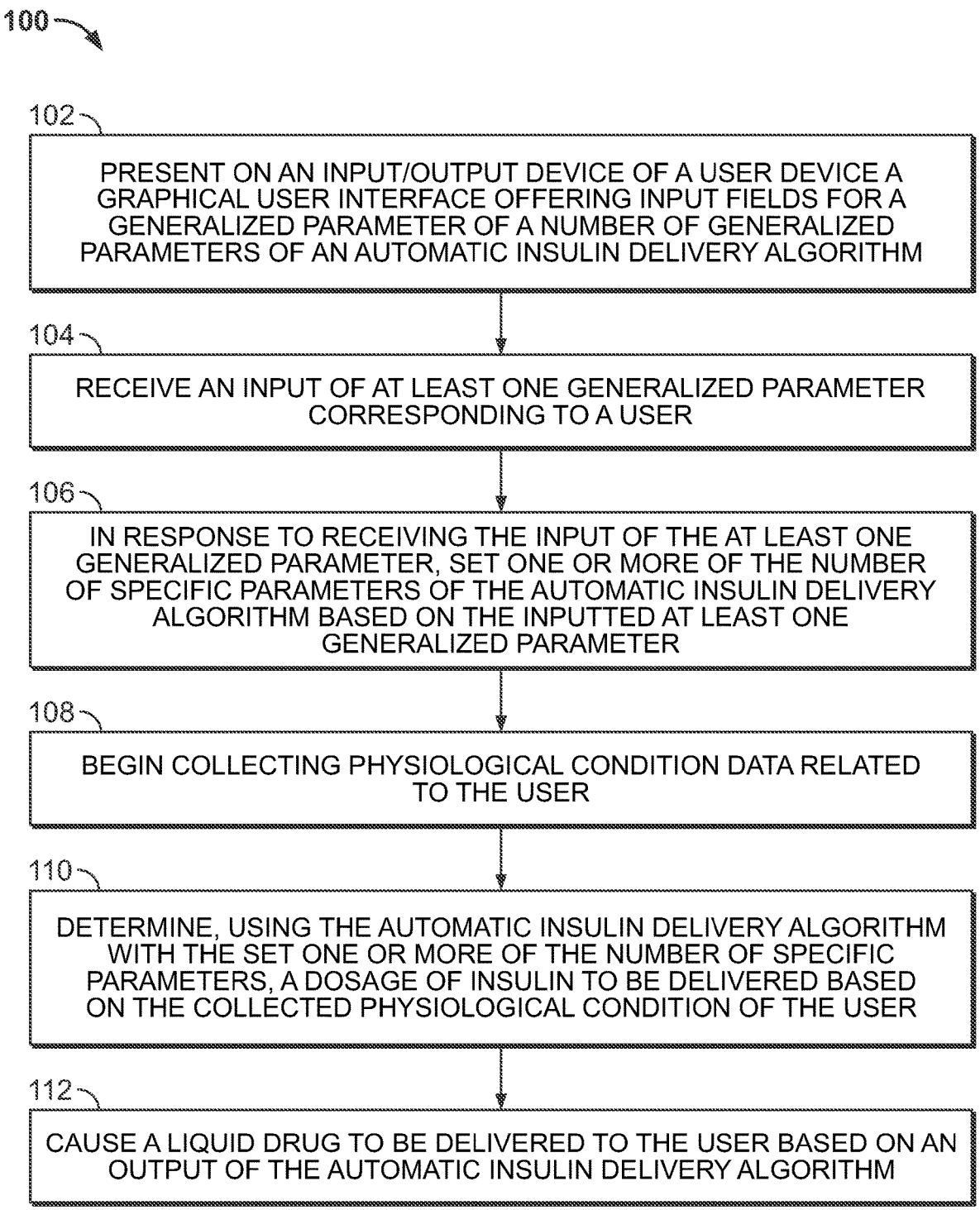
FIG. 1A illustrates a flowchart of an example of a simplified onboarding process that allows for simplified input of a number of generalized parameters.

FIG. 1A illustrates a flowchart of an example onboarding process that allows for simplified input of a number of generalized parameters. The inputted general parameters may be usable by an automated insulin delivery (AID) algorithm. Different parameters, input during an onboarding process of the user with the AID algorithm, may provide the AID algorithm with enough information that in combination with default settings enable a user to begin using a wearable drug delivery device.

Although users are not required to enter any clinical parameters, such as basal profile, IC ratio and/or Correction Factor, during the initial set up (i.e., onboarding) of their wearable drug delivery device, their health care providers may review available blood glucose outcomes and may consider that the users may need increased or decreased insulin delivery compared to default dosages of the AID algorithm.

The AID algorithm may use safety constraints to limit the effects of some inputs to the AID algorithm from the user for safety purposes.

In block 102, the routine 100 presents on an input/output device of a user device, such as a controller, a graphical user interface input offering input fields for a generalized parameter of a number of generalized parameters of an automated insulin delivery algorithm. For example, the number of generalized parameter(s) usable by the AID algorithm may be 1, 2, or up to 3-6, or the like. For example, a generalized parameter may be a user's weight, an age, a reference basal, an activity level, and/or a type of diet, gender, a type of diabetes (e.g., Type 1, Type 2, Gestational), and/or an equipment brand (e.g., equipment being an infusion pump, a continuous glucose monitor, a heart rate monitor, a fitness device, blood oxygen sensor, or the like). The number of generalized parameters, for example, is less than a number of specific parameters of the automated insulin delivery algorithm. Meanwhile, there may be a number of specific parameters. Examples of specific parameters may include a blood glucose measurement value, a value for a user's HbA1c, an estimated initial total daily insulin (TDI), a calculated TDI, a an upper boundary of insulin delivery, a baseline basal rate delivery of insulin, basal/bolus ratio, an insulin-on-board (IOB), or a combination of two or more of the foregoing. In block 104, the routine 100 receives an input of at least one generalized parameter corresponding to a user.

In block 106, the routine 100 in response to receiving the input of the at least one generalized parameter, sets one or more of the number of specific parameters of the automated insulin delivery algorithm based on the inputted at least one generalized parameter. For example, the specific parameters that may be set may include an estimated initial total daily insulin (TDI) amount, an upper boundary of insulin delivery, a basal/bolus ratio, or an insulin-on-board (IOB) amount, or a combination of two or more of the foregoing. For example, the AID algorithm may compare the inputted at least one generalized parameter to a threshold. Based on a result of the comparison, the AID algorithm may revise coefficients or elements of a cost function.

In block 108, the routine 100 may begin collecting physiological condition data related to the user, such as wirelessly via a blood glucose meter or a continuous glucose monitor, or directly from a user input. In block 110, the automated insulin delivery algorithm implementing the routine 100 may determine a dosage of insulin to be delivered based on the collected physiological condition of the user. The AID algorithm may be communicatively coupled to a pump mechanism or the like that is coupled to a user and that is operable to deliver insulin or other medication to a user. In block 112, the routine 100 may cause a liquid drug to be delivered to the user based on the determined dosage of insulin that is output from the AID algorithm.

Figure 1B:
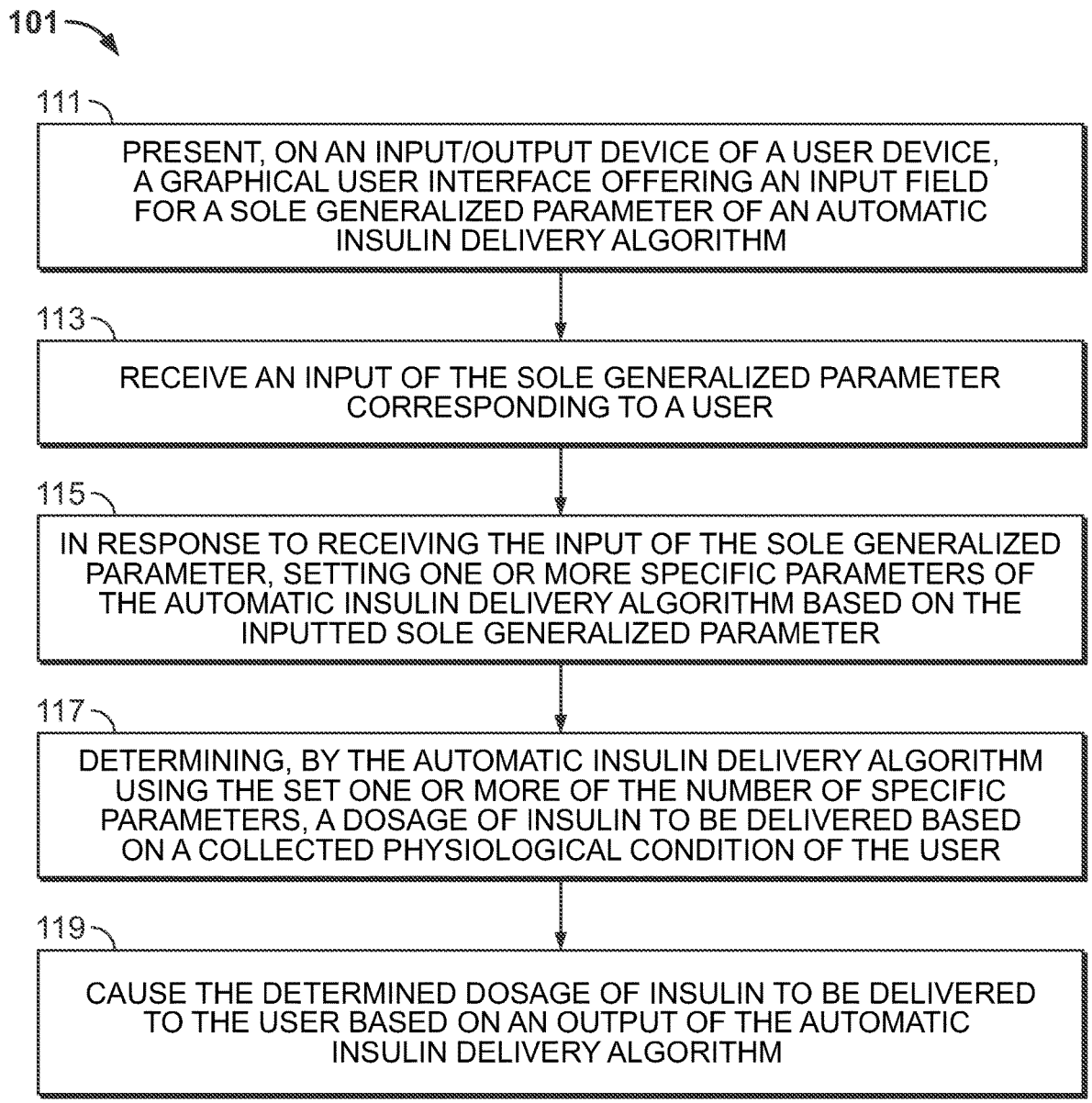
FIG. 1B illustrates a flowchart of another example of a simplified onboarding process that allows for simplified input of a sole generalized parameter.

It is also envisioned that the onboarding process may be further simplified to permit input of a sole generalized parameter, for example, a user's weight in kilograms or pounds. An example process flow of this further simplified onboarding process is illustrated in FIG. 1B and described below.

In the routine 101, an input/output device of a controller may present, at 111, a graphical user interface input offering an input field for a sole generalized parameter of an automated insulin delivery algorithm. In a specific example, the sole generalized parameter is a user's weight (which refers to a user's current weight). In block 113, the routine 101 receives the input of the sole generalized parameter.

In block 115, the routine 101, in response to receiving the input of the sole generalized parameter, sets one or more of the number of specific parameters of the automated insulin delivery algorithm based on the inputted sole generalized parameter. For example, when the sole generalized parameter is weight, the AID algorithm may calculate a TDI value based on the inputted weight. This TDI value may be an initial TDI estimate for the user based on the user's weight. Based on the calculated TDI value, the AID algorithm may set or revise other coefficients, parameters, or elements of a cost function or model.

In block 117, the automated insulin delivery algorithm implementing the routine 100 may determine a dosage of insulin to be delivered based on the collected physiological condition data. The AID algorithm may be communicatively coupled to a pump mechanism or the like that is coupled to the user and that is operable to deliver insulin or other medication to the user.

In block 119, the routine 101 may cause a liquid drug to be delivered to the user based on the determined dosage of insulin that is output from the AID algorithm.

After initial parameters are entered (e.g., weight), calculated (e.g., TDI based on weight), or set (e.g., parameters, coefficients, or elements of a cost function or model), the system may collect physiological condition data related to the user, such as wirelessly via a blood glucose meter or a continuous glucose monitor, or directly from a user input. The collected physiological condition data may be used by the system going forward to update the various parameters (e.g., modify the initial TDI estimate, which was based on the user's weight, up or down to more accurately reflect the user's medicament needs).

FIG. 2 illustrates an example of a graphical user interface of a user device that is suitable for implementing the example onboarding process of FIG. 1. Generalized parameters that may be useful for entry into the AID algorithm by the user may include a reference basal value, a user's age, a user's activity level, and a diet type.

Figure 2A:
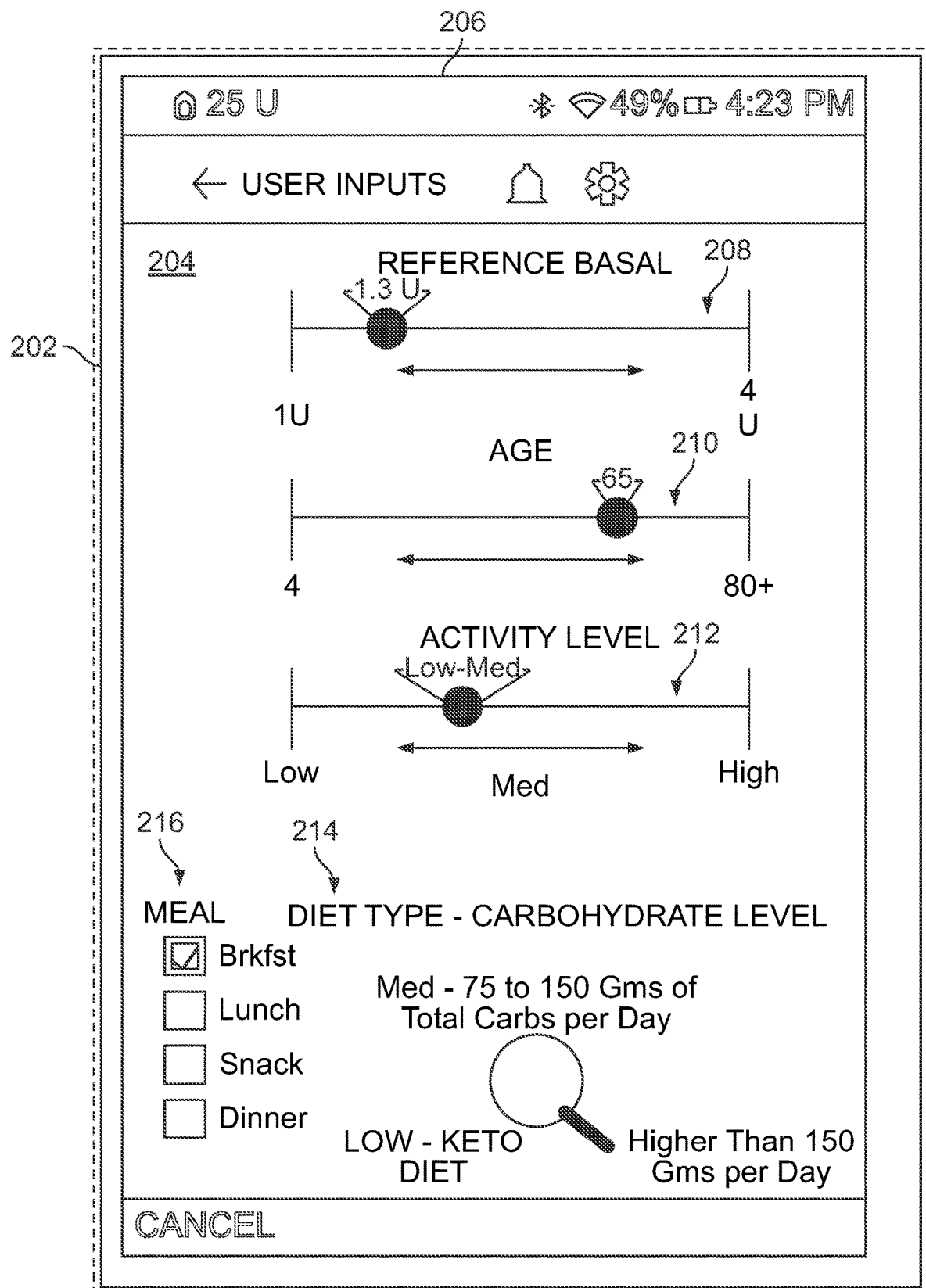
FIG. 2A illustrates an example of a graphical user interface suitable for implementing the example onboarding process of FIG. 1A.

As shown in FIG. 2A, a controller 202 may be operable to receive inputs from a user via an input/output device 206. The input/output device 206 may be a touchscreen as shown in FIG. 2 or may include one or more of a keyboard, a digital personal assistant, such as Alexa®, Siri®, Cortana® or Google Assistant®, a display, a speaker, or the like. The graphic user interface 204 may present one or more input fields for input of the generalized parameters. For example, a slider bar, a radio button, a touch button, a check box, or the like may be used as an input device to enter a respective generalized parameter. The controller 202 may be equipped with a processor that is operable to execute programming instructions to implement the input/output device 206 and also execute an automated insulin delivery algorithm. In the example of a reference basal value, the slider bar may be used as the input field for a reference basal input 208. An example value for reference basal may be between 1 and 4 Units that may be input as the reference basal input 208. Similarly, the age input 210 and the activity level input 212 may also be input via slider bars. An alternative, input/output device 206 may be a radio button that a user manipulates using a circular gesture to indicate selection of a diet type and indicate the diet type input 214 of the user. Another alternative may enable the user to indicate different diet types for individual meals, such as breakfast, lunch, snack or dinner via a meal indicator input 216, which may be a checkbox input, or the like. Each type of meal may correspond to a particular diet type, and the user may specify a diet type for each type of meal using the meal indicator input 216 and diet type input 214 sequentially for each type of meal.

Of course, other input devices may be used to enter the generalized parameter, such as a keyboard, mouse, stylus, voice recognition, or the like. In addition, all of the generalized parameters do not need to be entered. The graphic user interface 204 may present the respective inputs of the reference basal input 208, age input 210, activity level input 212, diet type input 214, and the meal indicator input 216 on separate screens that are presented sequentially after a user has an opportunity to either make the requested input or choose not to input the requested generalized parameter.

Figure 2B:
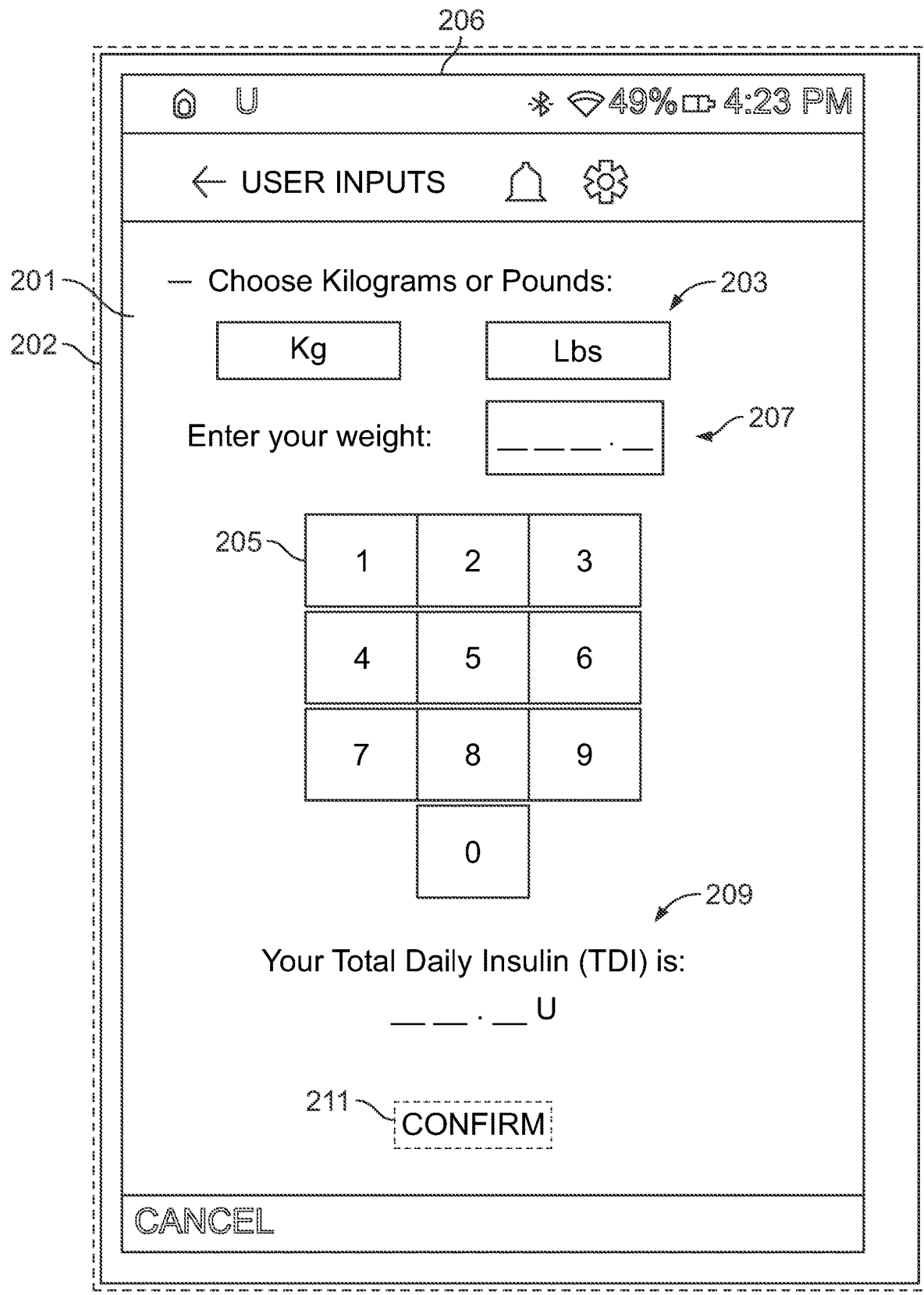
FIG. 2B illustrates an example of a graphical user interface suitable for implementing the example onboarding process of FIG. 1B.

The example of FIG. 2B illustrates a graphical user interface suitable for implementing an example onboarding process utilizing a sole generalized parameter. In FIG. 2B, the sole generalized parameter may be a user's weight. Alternatively, this user input may be used in conjunction with other user inputs (such as those depicted in FIG. 2A). But in one preferred embodiment, the user need only enter their weight for the system to be initialized and set up for delivering personalized medicament for the user.

For example, the controller 202 of FIG. 2B may be operable to receive inputs from a user via an input/output device 206. The input/output device 206 may be a touchscreen that is operable to present a graphical user interface 201. The graphical user interface 201 may present various prompts for a user to enter the sole generalized parameter. For example, prompt 203 may request a selection between kilograms or pounds for the units of the user's weight. Alternatively, the units of the inputted weight may be pounds or kilograms by default, depending on the user's geographic location, and the units may be displayed to the user. A numerical keypad 205 may be provided to allow the user to enter their weight. The presentation window 207 present the inputted user's weight and presentation window 209 may present an initial estimate of the user's total daily insulin (TDI) as calculated by the AID algorithm. As mentioned above, this initial TDI estimate may be used initially by the system to determine how much medicament (e.g., insulin) to deliver to the user initially, and may be changed over time based on blood glucose measurement data. An optional confirmation button 211 may be presented to allow the user to optionally confirm the presented initial TDI determination. In an alternative embodiment, the user may be allowed to change the initial TDI determination by tapping on the TDI amount in presentation window 209 and entering a new value (with a numerical keypad) or increasing or decreasing the initial TDI determination up or down (for example, with arrow keys). If the user changes the initial TDI determination, the modified value may be used as the initial TDI determination. Limitations or warnings may be applied to any changes the user attempts to make. For example, if the initial TDI determination based on the user's inputted weight was determined to be 42 Units of medicament, and the user attempts to change this value to 65 Units of medicament, the system may output an error or a confirmation screen to the user asking the user to either confirm the inputted TDI entry or confirm the user's inputted weight (and units). Alternatively, the system may only allow changes to the initial TDI determination up to certain threshold(s), such as 20% or 30% upward, and 40% or 60% downward; and if the user attempts to input a modified TDI amount in excess of the threshold(s), the system may output a message to the user and also change the modified TDI amount up to the threshold.

In an operational example, a user may be new to infusion pump therapy and may not know what TDI to use for their system. To accommodate these and other situations, this embodiment allows a user to only input their weight (e.g., in pounds or kilograms). If inputted in pounds, the programming code providing this function for the AID algorithm may convert the inputted weight in pounds to kilograms for purposes of determining an initial TDI estimate for the user; or, a different conversion factor may be used that corresponds to using pounds instead of kilograms such that no lb-kg conversion is necessary. In either case, a proper conversion factor will be used that corresponds to the units of the weight input by the user. The AID algorithm may use a predetermined factor to automatically calculate an initial TDI for the user. In an example, the TDI may be the only specific parameter that is set in response to the user's weight being input as the sole generalized parameter. For example, a multiplier may be applied to the user's weight. The multiplier may have a preselected value that is approximately equivalent to a steady state TDI value for a large population of users when multiplied by the user's weight. For example, a value of 0.6 may be used as the conversion factor or multiplier when the inputted weight is in kilograms. Alternatively, the multiplier may be preselected to be 0.3 or 0.2 (when the inputted weight is in kilograms) to result in a more conservative initial TDI estimate for the user. Other conversion factors or multipliers may be used. And corresponding conversion factors or multipliers may be used when the inputted weight is in units of pounds. By way of example, if the user indicates at 203 that their weight will be input in pounds and inputs a weight of 155 pounds, the routine may be operable to convert the 155 pounds to 70.3 kilograms. Based on the number of kilograms, the AID algorithm may automatically further calculate the user's starting or initial TDI as 42.2 Units (i.e., 70.3×0.6 is 42.2, which may be rounded to 42 Units in some embodiments). However, the 0.6 preselected multiplier may be considered too aggressive, so the preselected multiplier may be a more conservative value of 0.3 or 0.2. The multiplier may be preselected by the manufacturer of the drug infusion system.

Based on the calculated (and optionally confirmed) TDI, the AID algorithm further determines a basal delivery rate for the user, which may be based on a 1:1 basal/bolus ratio. For example, if the initial TDI estimate was determined to be 42 Units, the system may determine that 21 Units should be allocated to basal deliveries, and if this amount is delivered uniformly over 24 hours, the user would initially receive 0.875 Units of medicament per hour. Bolus dosages may also be calculated using this initial TDI estimate and the system's bolus calculator may rely (at least initially) on this initial TDI estimate when calculating how much medicament to deliver in response to meals or as correction boluses. As mentioned elsewhere in this disclosure, the initial TDI estimate may change over time to more accurately reflect the user's medicament needs. In other words, as additional data is gathered regarding the user (e.g., blood glucose measurement values), various system parameters, including a TDI for the user, may change over time. Additionally, or alternatively, if the user enters additional generalized parameters, the initial TDI estimate may increase or decrease based on the user's entries. But if no other parameters are entered by the user, the system may use the initial TDI estimate that is determined based on the sole input of the user's weight.

Figure 3:
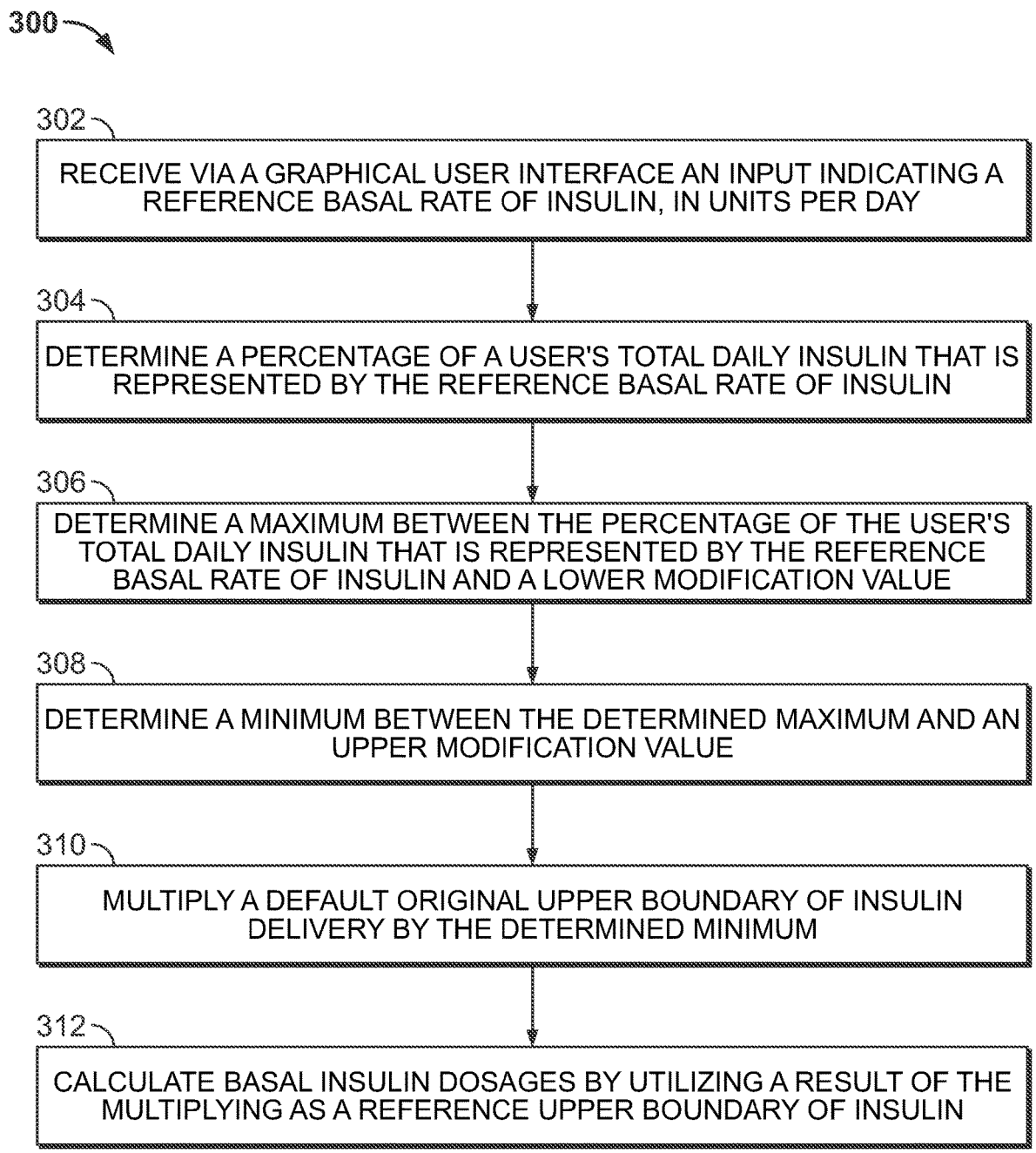
FIG. 3 illustrates a flowchart of an example process utilizing a generalized parameter input via the examples of FIG. 1 and FIG. 2.

FIG. 3 illustrates a flowchart of an example process utilizing a generalized parameter input via the examples of FIG. 1 and FIG. 2.

Reference basal may be a rate, such as a number of units (U) per hour, units per day, or the like. In an example, the AID algorithm may have a default basal rate setting of 1 U per hour. In block 302, the routine 300 receives via a graphical user interface, such as graphic user interface 204 of FIG. 2, an input indicating a reference basal rate of insulin (i.e., indicated by a Bref), in units per time period, such as hour or day. Based on this single input, other parameters may also be determined by the AID algorithm and managed by the system, such as amount and time of bolus dosages, recommended dosages and times of open-loop insulin deliveries, and the like.

In an example, automated delivery systems are operable to deliver a certain basal amount of insulin, and that amount of insulin is usually dependent on a default setting of 1 unit of insulin per hour, for example. In some situations, the user or healthcare provider may enter 1.5 U per hour, which is a 50% increase over the 1 unit per hour default setting. However, an upper boundary safety constraint may limit the basal insulin delivery to, for example, 1.2 U per hour as shown in the following equation. In other words, the percentage increase may be limited to 20% (i.e., 100×0.2) in this example. Of course, the percentage increase boundary may be tunable. The degree of tunability may be based on additional details related to the user, such as age, weight, gender and the like. The user or the healthcare provider can input an estimate of the user's basal rate as a reference basal for use as a generalized parameter by the AID algorithm.

In block 304, a processor executing routine 300 as part of the AID algorithm may determine a percentage of a user's total daily insulin that is represented by the reference basal rate of insulin. In response to the input of the reference basal, the AID algorithm may determine an upper boundary for the amount of insulin that is to be delivered so a user does not over deliver insulin.

The reference basal rate parameter Bref (as described in more detail below) may be input by a user into the AID algorithm. In one example, the reference basal rate parameter $B_{ref}$ may be input by the user as a single parameter, which the user may track and may be input to the AID algorithm as described herein. Alternatively, the user at onboarding may set their TDI as a default, or alternatively, the user may input a TDI value that was calculated for the user by a clinician and the system based on the inputted TDI value may calculate a $B_{ref}$ value for use by the AID algorithm as described herein.

Although users are not required to enter any clinical parameters, such as basal profile, IC ratio and/or Correction Factor, their health care providers may review the glucose outcomes and may consider that the users may need increased or decreased insulin delivery compared to the average AID insulin deliveries. The users and/or HCPs can then provide this reference basal, $B_{ref}$, to the AID system's algorithm. The AID algorithm may be operable to modify the maximum delivery constraint, upper boundary $UB_{original}$, of the AID algorithm based on this $B_{ref}$ as follows:

$$UB_{ref} = UB_{original} \cdot \min\left(\max\left(\frac{B_{ref}}{0.5 \cdot TDI}, \text{lower mod. value}\right), \text{upper mod. value}\right) \quad \text{Equation 1}$$

where $UB_{original}$ is the maximum delivery constraint for insulin to be delivered over the course of a day, the lower modification (mod.) value is a minimum factor that modifies $UB_{original}$ the least amount, the upper modification (mod.) value is a maximum factor that modifies $UB_{original}$ the greatest amount, and $B_{ref}$ divided by 0.5×TDI represents the ratio of user basal ($B_{ref}$) to the nominal TDI basal (0.5×TDI).

In an example, Equation 1 may be used during an onboarding process. In an onboarding example, the TDI value in Equation 1 may be a system generated TDI. In an example, TDI is specific parameter that may be set by the AID algorithm based on a user input during onboarding. For example, the AID algorithm may generate a TDI based on a user's insulin history. If a user's insulin history does not exist, the TDI may be generated based on a user weight-based calculation. For example, a user when onboarding may enter their weight as a sole generalized parameter, the AID algorithm may generate an estimated TDI based on the weight and the estimated TDI may be set as the TDI for use by the AID algorithm to generate insulin dosages for delivery to the user. The AID algorithm may update the TDI as the AID algorithm gains additional information.

Also, during the example of the onboarding process that utilizes the input of multiple generalized parameters, in addition to the user entering their weight, the user may enter a $B_{ref}$ value. In the routine 300 at block 306, the processor may determine a maximum value between the percentage of the user's total daily insulin that is represented by the reference basal rate of insulin (i.e., $B_{ref}$ divided by (0.5× TDI)) and a lower modification value (i.e., lower mod. value of Equation 1). In an operational example, the AID algorithm, using Equation 1, may determine a maximum value between the entered $B_{ref}$ value divided by half of the user's TDI (i.e., 0.5 times the user's TDI) and a lower modification threshold value (i.e., lower mod. value in Eq. 1 above), such as 0.8 or the like.

In block 308, the routine 300 may determine a minimum between the determined maximum and an upper modification value. For example, in response to determining the maximum value, the AID algorithm may utilize a minimum function to evaluate the determined maximum value against an upper modification threshold value (i.e., upper mod. value in Eq. 1 above), such as 1.2 or the like. The outcome of the evaluation of the minimum function may provide a modification factor that may be used to modify the original upper boundary, $UB_{original}$. The minimum function is formulated to provide a value that may be between 0.8 and 1.2 based on the example lower and upper modification factors provided above.

In block 310, the routine 300 may multiply a default original upper boundary of insulin delivery by the determined minimum. Continuing with the operational example, the original upper boundary, $UB_{original}$ may be a value, such as 4 Units of insulin. Assume in the example that the minimum function returned a value of 0.9, the reference upper boundary, $UB_{ref}$, may be $UB_{original}$ times 0.9. Or, using the example value of 4 U for $UB_{original}$, $UB_{ref}$ is 4 U times 0.9, which equals 3.6 U. Using the example values for the lower modification threshold value (e.g., 0.8) and the upper modification threshold value (e.g., 1.2) and the example 4 U for the original upper boundary (i.e., $UB_{original}$), an example range of the reference upper boundary of insulin (i.e., $UB_{ref}$) may be between 3.2 U and 4.8 U.

In block 312, the processor executing routine 300 may use a result of the multiplying (i.e., $UB_{ref}$) to calculate basal insulin dosages. When the basal insulin dosages are calculated, the processor upon executing the AID algorithm may cause a wearable drug delivery device to deliver the calculated basal insulin dosages to a user, for example, as part of a diabetes treatment plan.

Different processes may be implemented in response to the other generalized parameters entered by the user.

Figure 4:
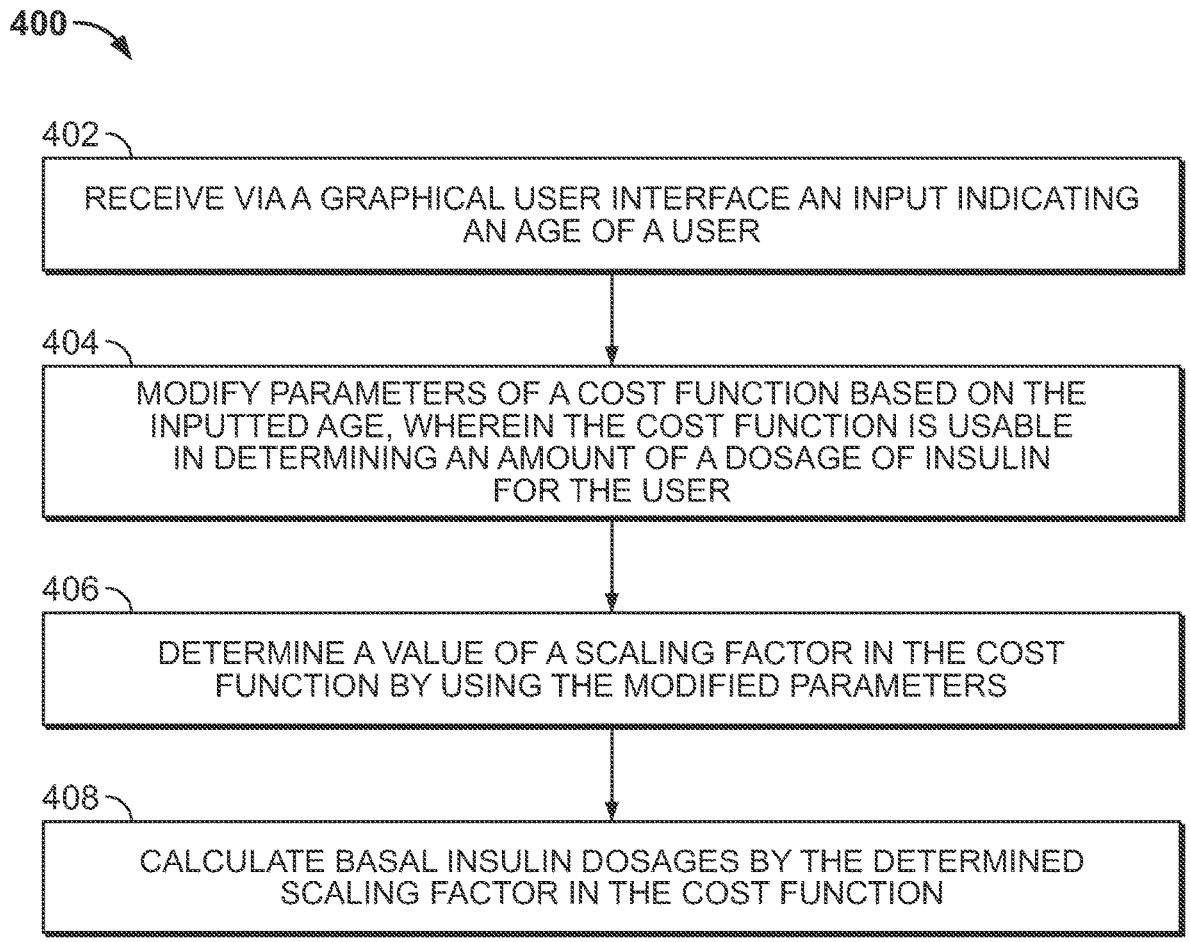
FIG. 4 illustrates a flowchart of an example process utilizing particular generalized parameter input via the examples of FIG. 1 and FIG. 2.

FIG. 4 illustrates a flowchart of an example process utilizing a generalized parameter input via the examples of FIG. 1 and FIG. 2. The graphical user interface for the AID algorithm may provide an optional Age entry that enables the insulin cost function to be modified based on a user's age. For example, the AID algorithm may modify the cost function when the age entry to the graphical user interface is lower than a certain threshold, such as 6 years old. The AID algorithm may determine dosages of insulin to be delivered based on minimizing a cost function. The cost function may be manipulated using a pair of weighted coefficients.

An example of a general parameter for input, such as age, may be used when younger children are the user of the wearable drug delivery device. Based on the generalized parameter of the child's age, the routine 400 may modify the calculation of one of the weighted coefficients. For example, healthcare providers may particularly desire to make a fine-tuned adjustment of the AID algorithm because the impact of the pump resolution may cause significant variations in insulin needs for the very low total daily insulin (TDI) amounts of younger children (e.g., the 0.05 U pump resolution versus 5 U of TDI=1% variation based on a single pulse of insulin). To limit the potential for wide variations in TDI, the AID algorithm may include an input field in a graphical user interface for entry of an age of the user, such as age input 210 of FIG. 2. For example, the entered age may be compared to a certain threshold, such as 6 years of age. If the entered age is lower than the certain threshold, such as 6, the AID algorithm may decrease, for example, a minimum scaling rate of insulin costs to a lower value.

As mentioned above, one or more of the generalized parameters may cause the AID algorithm to adjust the cost function to address one or more conditions that may be influenced by the one or more generalized parameters. As a starting point, it is helpful to review a typical conventional cost function. A typical formulation for cost J is:

$$J = Q \cdot \sum_{i=1}^{M} G_p(i)^2 + R \cdot \sum_{i=1}^{n} I_p(i)^2 \quad \text{Equation 2}$$

where Q and R are the pair weighted coefficients mentioned above. The factor $$G_p(i)^2$$

is the square of the deviation between the projected blood glucose level for an insulin dosage at cycle i and the projected blood glucose level for the basal insulin dosage, and M is the number of cycles in the prediction horizon.

The factor $$I_p(i)^2$$

is the square of the deviation between the projected insulin delivered at cycle i and the insulin for basal insulin delivery, and n is the control horizon in cycles.

Thus, the factor:

$$Q \cdot \sum_{i=1}^{M} G_p(i)^2$$

is the weighted glucose cost, and the factor:

$$R \cdot \sum_{i=1}^{n} I_p(i)^2$$

is the weighted insulin cost. The total cost J is the sum of the weighted glucose cost and the weighted insulin cost. A cycle has a fixed interval, such 5 minutes.

The coefficient R, referred to as "a scaling rate of insulin," is a tunable value that may affect the total cost J and that is based on delivery of insulin. Healthcare providers may particularly desire to have fine-tuned adjustment of AID systems for younger children, such as those around the age of 5-7. One example of the generalized parameters is age, and the AID algorithm may modify the coefficient R based on age. In the Equation 2, the example age is 6, but other ages for children may also be considered. Young children simply need less insulin than teen aged children or adults. A drug delivery device in a single pulse of the pump mechanism (also referred to as the "pump resolution") may deliver 0.05 Units of insulin to a user. When one considers that a total daily amount of insulin (i.e., TDI) for young children may be 5 Units, the pump resolution (of 0.05 U) as compared to a TDI of 5U represents a 1% variation based on the single pulse of the pump mechanism. As a result, changes in the number of pulses of the pump mechanism may cause significant variations in insulin needs for users that function with very low TDI, such as younger children. Therefore, it is beneficial to be more conservative for people with low TDI—for example, people who are younger because small changes in the amount of insulin delivered by the pumps to young users may have a significant impact on the young user's TDI.

In the cost function, the scaling rate of insulin R may include an aggressiveness factor having an approximate value 9000 that may be used for users with mid-range TDI and that represents an adjusted weight on insulin deviation versus glucose deviation. The higher value of the aggressiveness factor, the more heavily the AID algorithm penalizes the insulin deviation versus any glucose excursions. In a standard implementation, the aggressiveness factor is fixed. However, the aggressiveness of the scaling rate of insulin R may be attenuated to accommodate the needs of younger users.

The graphical user interface for the AID algorithm may provide an optional age entry that enables the insulin cost function to be modified based on a user's age. For example, the AID algorithm may modify the cost function when the age entry to the graphical user interface is lower than an age threshold, such as 6. As shown in Equation 3 below, the AID algorithm may decrease the minimum scaling rate of insulin (i.e., coefficient R) to a lower value, as follows:

$$R_{hi} = \begin{cases} 9000 \cdot \left(\frac{41}{\max(\min(TDI, 10.25), 61.5)}\right)^2 & \text{Age} > 6 \\ 9000 \cdot \left(\frac{41}{\max(\min(TDI, 8.2), 61.5)}\right)^2 & \text{Age} \leq 6 \end{cases} \quad \text{Equation 3}$$

where, in this example, the value 41 is the TDI of a "standard" patient, who has an unmodified $R_{hi}$ of 9000. Patients having another TDI value may have their $R_{hi}$ scaled, for example, according to the inverse square law, but the scaling may be set stop at a maximum TDI, for example, of 61.5 at the high end and a TDI of 10.25 or 8.2, for example, at the low end for users over 6 years of age or equal to 6 or under, respectively.

The AID algorithm may process the inputted age according to routine 400. In routine 400, if the user's age is greater than the age threshold, the AID algorithm may as the user's TDI goes down—e.g., below an over-age threshold, such as 10.25 units or the like, the aggressiveness factor may be increased. For example, the value $R_{hi}$ directly feeds into the cost function of Equation 2 as a substitute for the value R. But typically, algorithms have a scaling aggressiveness, where the higher the TDI is the more aggressive the AID algorithm is designed to behave, and vice versa. If a user has a low TDI, the AID algorithm still aims to be aggressive but is more conservative (e.g., changes have lesser magnitudes and are less drastic) when the user's TDI is mid-range.

In an operational example, the routine 400 receives via a graphical user interface an input indicating an age of a user at block 402. In block 404, the routine 400 modifies parameters of a cost function based on the inputted age. The cost function of Equation 2 is usable by the AID algorithm to determine an amount of a dosage of insulin for the user. In block 406, the routine 400 determines a value of a scaling factor in the cost function by using the modified parameters. Based on a value of the age input, the AID algorithm may determine the scaling factor differently. For example, the AID algorithm executing routine 400 at block 406 may in response to the age of the user being greater than an age threshold, determine a minimum between an over-age constant and the user's total daily insulin value. The AID algorithm may determine a maximum between the determined minimum and a delivery threshold. A timing threshold may be divided by the determined maximum and the quotient may be squared. A default scaling factor value may be multiplied by a result of the squaring, where the result is the value of the scaling factor. Alternatively, at block 406, the AID algorithm may, in response to the age of the user being less than or equal to an age threshold, determine a minimum between an underage constant and the user's total daily insulin value. A maximum between the determined minimum and a delivery threshold may be determined. The AID algorithm may divide a timing threshold by the determined maximum. squaring the quotient of the division and multiplying a default scaling factor value by a result of the squaring, where the result is the value of the scaling factor.

In block 408, the routine 400 calculates basal insulin dosages by the determined scaling factor in the cost function. The AID algorithm may generate signals that cause the calculated basal insulin dosages from block 408 to be delivered to the user via a wearable drug delivery device.

Other technical features may be readily apparent to one skilled in the art from the following figures, descriptions, and claims.

Figure 5:
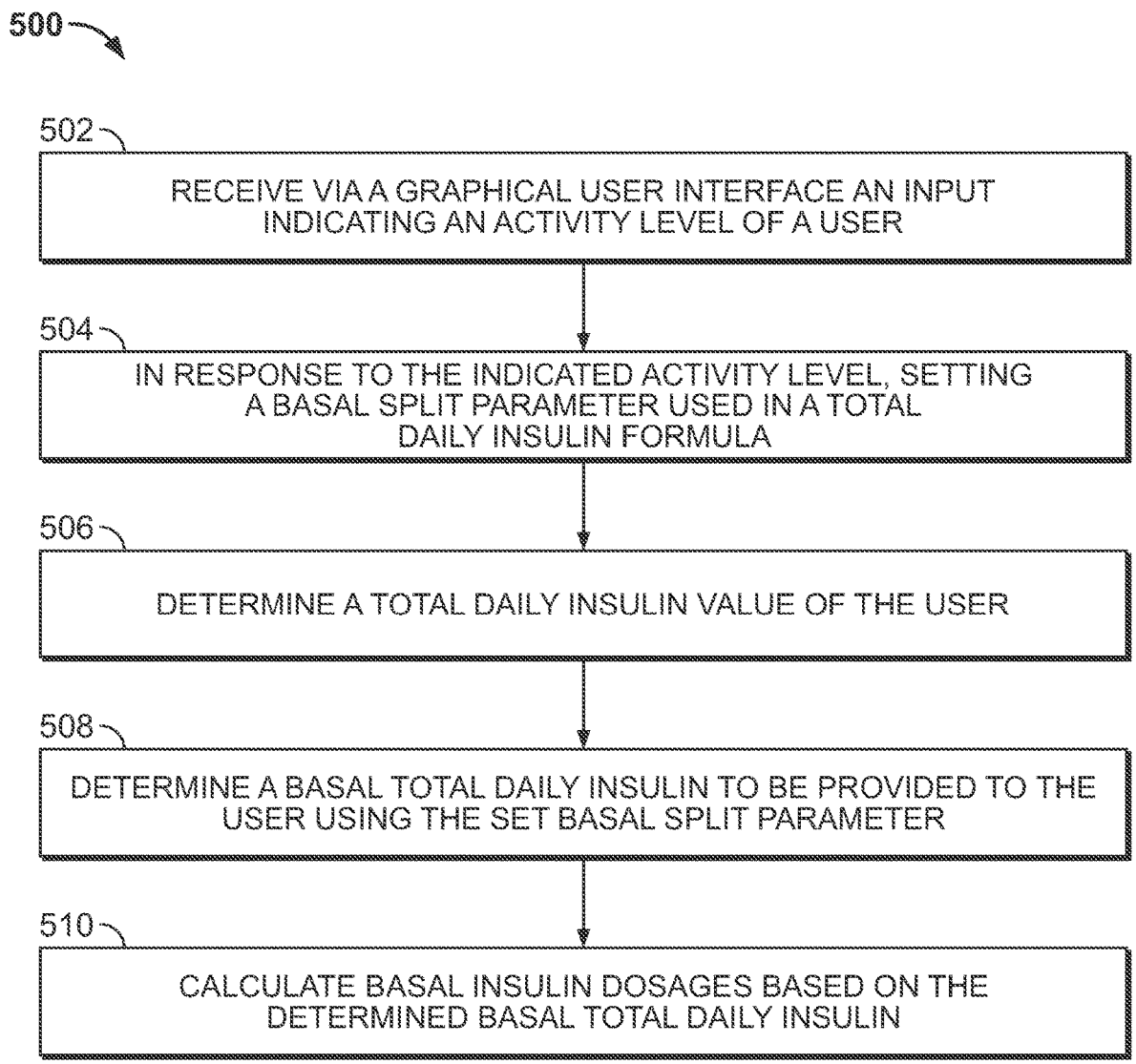
FIG. 5 illustrates a flowchart of an example process utilizing another particular generalized parameter input via the examples of FIG. 1 and FIG. 2.

FIG. 5 illustrates a flowchart of an example process utilizing a further generalized parameter input via the examples of FIG. 1 and FIG. 2.

A common rule of thumb is a 50/50 split of insulin delivery provided via basal and bolus dosages, respectively. In other words, half of the user's total daily insulin is provided by basal dosages and the other half is provided by bolus dosages. An active user when participating in activities typically needs less insulin since during activity their cells are more sensitive to insulin and the uptake of insulin is more efficient.

The graphical user interface for the AID algorithm may provide an activity level input 212 entry that enables the determination of insulin dosages to be modified. Users that execute a high level of activity may use significantly less basal insulin compared to those who have less active lifestyles. In these cases, the user or healthcare provider may indicate to the system that they want to cover an insulin amount less than 50% of their total insulin as basal. For example, the AID algorithm may modify the basal/bolus split based on the inputted activity level input 212.

This Basal/bolus Split, $S_{Basal}$, can be set to a lower value, such as 40% for high activity users, instead of 50% for standard activity users if users indicate this trigger when inputting the generalized parameters. The AID algorithm may determine the basal split parameter, $S_{basal}$, based on the activity level input 212 according to the following tunable settings:

$$S_{basal} = \begin{cases} 0.5 & \text{Standard Activity} \\ 0.4 & \text{High Activity} \end{cases}$$

Basal split parameter

The AID algorithm may determine the basal TDI amount based on the following calculation:

$$\text{Basal}_{TDI} = S_{basal} \cdot TDI \qquad \text{Equation 3}$$

In alternate embodiments, the 0.4 value for high activity can be made variable between a range, such as 0.35 to 0.5, based on the user's draggable setting of activity level input 212 of FIG. 2.

In an operational example, the routine 500 may be operable at block 502 to receive via a graphical user interface an input indicating an activity level of a user. This setting may be cross-checked with an accelerometer accessible to the AID algorithm. For example, if the user is not active for several hours (e.g., 3 hours, 4 hours, 5 hours, or 6 hours), the AID algorithm may be operable to generate an alert that the user's basal split value is less than 50% and might need adjusting.

In block 504, the AID algorithm executing the routine 500 may be operable, in response to the indicated activity level, to set a basal split parameter used in a total daily insulin formula.

In block 506, the AID algorithm executing the routine 500 may determine a total daily insulin (TDI) value of the user. The determination of TDI may be based on age, physiological condition information received from user or the like.

In block 508, the routine 500 may enable determination of a basal total daily insulin amount to be provided to the user.

In block 510, the routine 500 may calculate basal insulin dosages based on the determined basal total daily insulin. The AID algorithm may generate signals that cause the calculated basal insulin dosages from block 510 to be delivered to the user via a wearable drug delivery device.

Other technical features may be readily apparent to one skilled in the art from the following figures, descriptions, and claims.

Figure 6:
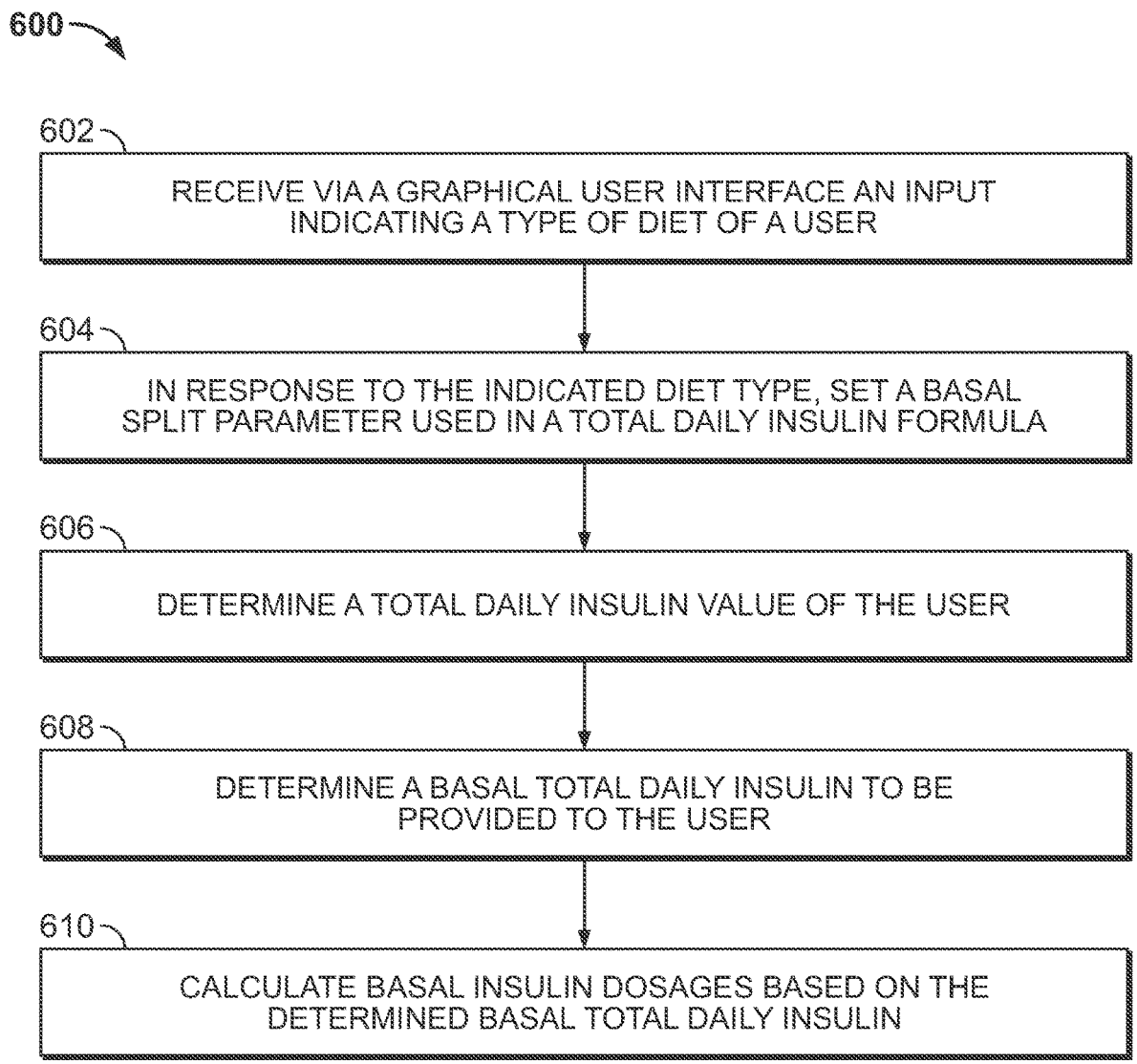
FIG. 6 illustrates a flowchart of an example process utilizing yet another particular generalized parameter input via the examples of FIG. 1 and FIG. 2.

The basal split parameter may also be modified based on the input of yet another generalized parameter in the graphic user interface 204 of FIG. 2. FIG. 6 illustrates a flowchart of an example process utilizing yet another particular generalized parameter input via the examples of FIG. 1 and FIG. 2. This generalized parameter is for a type of diet. For example, some users may adhere to non-standard diets, such as a Keto (low carbohydrate) diet, that may require significantly higher basal insulin delivery amounts (relative to bolus insulin delivery amounts) as compared to standard dietary lifestyles that are higher in carbohydrate intake. The AID algorithm may enable the user to indicate a type of diet or at least offer an option to indicate a non-standard diet.

If you are not eating carbohydrates, the need for bolus insulin is reduced but the need for basal insulin may increase to cover overall insulin needs of the user. Users that partake in non-standard diets may instead require significantly higher basal compared to standard lifestyles, such as in a keto diet. For example, if the user indicates a keto diet, the basal split parameter $S_{basal}$, which is a tunable parameter, can be set to a higher value, such as 60%, instead of 50% as shown below:

$$S_{basal} = \begin{cases} 0.5 & \text{Standard Diet} \\ 0.6 & \text{Keto (Low Carb) Diet} \end{cases}$$

Because the user is not ingesting as many carbohydrates with a low carbohydrate diet, the relative amount of basal insulin increases, as the required amount of insulin delivered via bolus dosages goes down. As mentioned, the basal split parameter is tunable, for example, the diet type input 214 may cause the basal split parameter to range between 0.65 to 0.5 instead of being fixed at 0.6 based on user's draggable setting of relative amount of carbohydrate ingestion.

The AID algorithm may, in response to the basal amount being greater than a threshold, generate a prompt on the graphic user interface 204 of FIG. 2 asking the user if they are still on the low carbohydrate diet.

During onboarding processes at the set up for a wearable drug delivery device, the use of generalized parameters enables users to input simpler values as compared to the intimidating calculations performed by diabetes healthcare professionals while still enabling the AID algorithm to establish an insulin delivery regimen for the user.

In an operational example, the routine 600 may be operable at block 602 to receive via a graphical user interface an input indicating a type of diet of a user.

In block 604, the processor executing the routine 600, in response to the indicated diet type, may set a basal split parameter used in a total daily insulin formula.

In block 606, the processor executing the routine 600 may determine a total daily insulin value of the user.

In block 608, the processor executing the routine 600 may determine a basal total daily insulin to be provided to the user.

In block 610, processor executing the routine 600 calculates basal insulin dosages based on the determined basal total daily insulin. The AID algorithm may generate signals that cause the calculated basal insulin dosages calculated at block 610 to be delivered to the user via a wearable drug delivery device.

Figure 7:
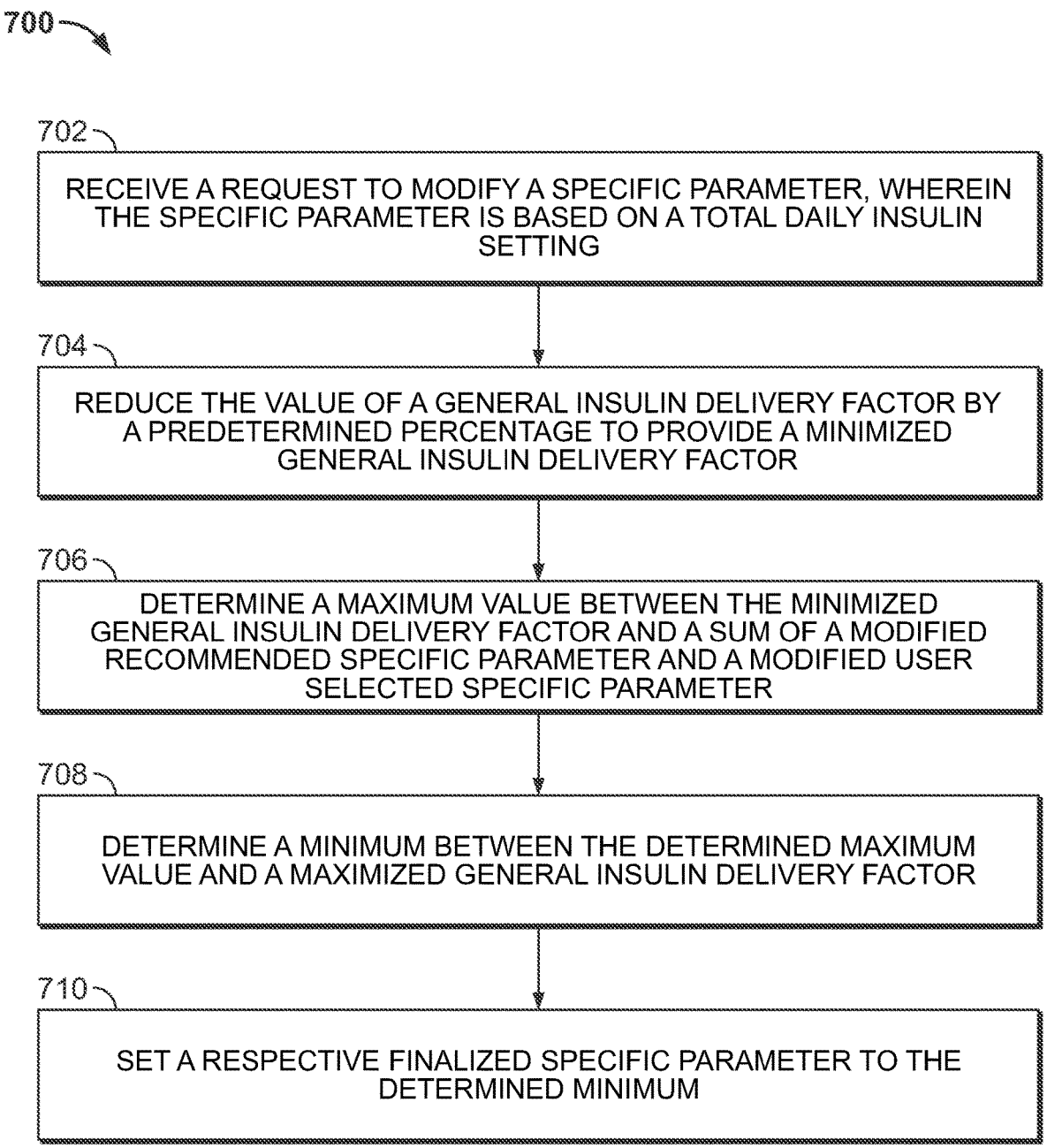
FIG. 7 illustrates a flowchart of an example process that determines a finalized setting of a specific parameter.

FIG. 7 illustrates a flowchart of an example process that determines a finalized setting of a specific parameter.

The earlier examples discuss the generalized parameters that a user may input that are used by the AID algorithm to modify a setting of one or more specific parameters.

In this example, the AID algorithm may initially calculate specific parameters of a user's insulin delivery regimen, such as a user's typical basal dosage value (e.g., $B_{auto}$), correct factor (CF) value (e.g., $CF_{auto}$), and Insulin-to-carbohydrate (IC) ratio value (e.g., $IC_{auto}$), automatically based on the user's total daily insulin needs in the user's available treatment plan history.

In operation, the AID algorithm may use the following equations to automatically set the respective specific parameters based on a user's total daily insulin (TDI) setting for operation of the user's wearable drug delivery device:

$$B_{auto} = 0.5 \cdot \frac{TDI}{24} \qquad \text{Equation 4}$$

$$CF_{auto} = \frac{1800}{TDI} \qquad \text{Equation 5}$$

$$IC_{auto} = \frac{450}{TDI} \qquad \text{Equation 6}$$

The parameter values of Equations 4, 5 and 6 may be default settings for each of the respective specific parameters. Equation 4 is an example of an automatic basal delivery amount, Equation 5 is an example of a correction factor, and Equation 6 is an example calculation of a user's insulin-to-carbohydrate ratio.

Equation 4 determines an hourly basal rate of insulin delivery $B_{auto}$ based on a rule of thumb related to TDI mentioned in an earlier example related to the basal split parameter. As an initial or default basal split parameter setting, the AID algorithm may utilize 50% or 0.5 as the basal split parameter. In this case, the automatic basal setting is determined according to Equation 4 in which the user's TDI is divided by the number of hours in a day (24) and the quotient is multiplied by the initial or default basal split parameter (0.5). The parameter $B_{auto}$ is the default amount of basal that is provided by basal delivery and the other 50% is provided by bolus deliveries of insulin.

Equation 5 is a correction factor $CF_{auto}$ that is used by the AID algorithm to estimate how much a user's blood glucose drops for each unit of insulin. The correction factor $CF_{auto}$ may be calculated differently for fast-acting insulin and for regular insulin. For example, Equation 5 illustrates the correction factor calculation based on the use of short-acting insulin, which is referred to as the "1800 rule." For example, if a user takes 30 Units of short-acting insulin daily, the user's correction factor is determined by dividing 1800 by 30, which equals 60. The result (e.g., 60) means the user's insulin sensitivity factor is 1:60, or that one unit of short-acting insulin is expected to lower the user's blood glucose by about 60 mg/dL. For regular insulin, a "1500 rule" in which the value 1500 is substituted for the value 1800 of the "1800" rule may be used to determine a user's correction factor.

Equation 6 is an example calculation of a user's insulin-to-carbohydrate ratio $IC_{auto}$, which is an amount of insulin used to lower the user's blood glucose from a particular amount of carbohydrates the user consumed. The particular calculation of Equation 6 may be used to determine the number of grams of carbohydrates that are approximately covered by 1 unit of insulin. The factor in the numerator, 450, is used when the user controls their diabetes with regular insulin, while a factor of 500 is used when the user controls their diabetes with fast-acting insulin.

These values $B_{auto}$, $CF_{auto}$, and $IC_{auto}$ may then subsequently be automatically adapted based on the changes in the user's insulin needs over time. In addition, a user may desire to make changes to these automatically-generated parameters, $B_{auto}$, $CF_{auto}$, and $IC_{auto}$, for more aggressive or less aggressive insulin deliveries both via the AID algorithm.

An example of a formula to calculate a daily insulin delivery factor may be a calculation of an amount of insulin that was delivered to the user per hour over the course of a period of time, such as the previous week (hence, the division by 7) is provided below.

$$\left(\sum_{i=1}^{7} TDI_i\right)/7$$

daily Insulin delivery factor where the 7 in the numerator indicates the number of days in a week and i is for each day of the previous 7 days.

The daily insulin delivery factor may be a calculation of an amount of insulin that was delivered to the user per hour over the course of a period of time, such as the previous week (hence, the division by 7) via basal insulin delivery:

$$\frac{\left(\sum_{i=1}^{7} TDI_i\right)/7}{48}$$

hourly basal Insulin Delivery Factor where the 7 in the numerator indicates the number of days in a week, the denominator value of 48 is the result of 24 times 0.5, where 24 represents the number of hours in a day and 0.5 represents the percentage amount of insulin received by the user via basal delivery. The expectation is that the user receives half (i.e., 0.5 or 50%) of their insulin need via basal delivery and the other half (i.e., 0.5 or 50%) via bolus deliveries.

The AID algorithm may be operable to consider the typical accepted clinical ranges in insulin delivery, and incorporate the user's changes as a mix of the user's current average insulin needs in, for example, the previous week, the user's suggested insulin changes may be implemented using the following parameter calculations:

$$B_{final} = \min\left(\max\left(0.8 \cdot 0.4 \cdot \frac{\left(\sum_{i=1}^{7} TDI_i\right)/7}{48}, 0.6 \cdot B_{auto} + 0.4 \cdot B_{user}\right), 1.2 \cdot 0.6 \cdot \frac{\left(\sum_{i=1}^{7} TDI_i\right)/7}{48}\right)$$ Equation 7

$$CF_{final} = \min\left(\max\left(0.8 \cdot \frac{1600}{\left(\sum_{i=1}^{7} TDI_i\right)/7}, 0.6 \cdot CF_{auto} + 0.4 \cdot CF_{user}\right), 1.2 \cdot \frac{2200}{\left(\sum_{i=1}^{7} TDI_i\right)/7}\right)$$ Equation 8

$$IC_{final} = \min\left(\max\left(0.8 \cdot \frac{400}{\left(\sum_{i=1}^{7} TDI_i\right)/7}, 0.6 \cdot IC_{auto} + 0.4 \cdot IC_{user}\right), 1.2 \cdot \frac{550}{\left(\sum_{i=1}^{7} TDI_i\right)/7}\right)$$ Equation 9

In the maximum function of Equation 7, the first term of—upper bound—0.8 and 0.4 that are used to reduce the insulin delivery factor (as shown above)—where 0.4 is considered the lowest feasible basal dosage boundary considering TDI. For example, a worst case basal/bolus split is 40:60, thus the value 0.4 or 40%. The AID algorithm may further reduce the 40% basal split by 20% by multiplying by 0.8. The AID algorithm sets the upper and the lower bounds at expected values based on insulin history. The second term of the maximum function (or overall middle term) (i.e., 0.6 $B_{auto}$+0.4 $B_{user}$) is an automated calculation that considers a user's input value (with a user trust of, for example, 40%). The first term and third term are the upper and lower bounds.

In Equation 7, the min/max envelopes may be typical ranges of each of the heuristics utilized by healthcare providers to estimate a user's insulin delivery parameters and may be allowed to be exceeded by up to 20% to account for changes in a user's lifestyle. The user's judgment may be trusted to a point of 40%, in the example. However, the user's judgment may be relied upon to a reasonable margin based on usage history and the like.

Equation 8 similarly accounts for user settings when calculating a final correction factor, $CF_{final}$. As shown in Equation 5, the correction factor is commonly calculated with 1800 in the numerator. In the determination of $CF_{final}$ in Equation 8, a value less than 1800, such as the 1600, may work better when basal insulin dosages make up less than 50% of the TDI. In addition, a value greater than 1800, such as 2200, may provide values that are better for those whose basal doses make up more than 50% of their TDI.

Equation 9 also is configured to account for user settings when calculating a final insulin-to-carbohydrate ratio, $IC_{final}$. The insulin to carbohydrate ratio is frequently calculated using a value of 400 in the numerator, but may also use values such as 450, 500, 550, 600 or other clinically relevant value.

In an embodiment, these adjustments can be implemented "behind the scenes" and impact automated components of insulin delivery, such as the AID algorithm and suggested boluses. In another embodiment, these adjustments can be proposed to the users via a prompt in a graphical user interface, such as graphic user interface 204, and the users can make further changes as desired. In this embodiment, the graphical user interface may present a setting with an input that the user may toggle to override ("reset") the adapted settings of the AID algorithm and force the AID algorithm to start adapting based on the user's input settings.

In an operational example, the routine 700 at block 702 receives a request to modify a specific parameter, wherein the specific parameter is based on a total daily insulin setting. In block 704, the routine 700 reduces the value of a general insulin delivery factor by a predetermined percentage to provide a minimized general insulin delivery factor. In block 706, the routine 700 determines a maximum value between the minimized general insulin delivery factor and a sum of a modified recommended specific parameter and a modified user-selected specific parameter. In block 708, the routine 700 determines a minimum between the determined maximum value and a maximized general insulin delivery factor. In block 710, the routine 700 sets a respective finalized specific parameter to the determined minimum.

Figure 8:
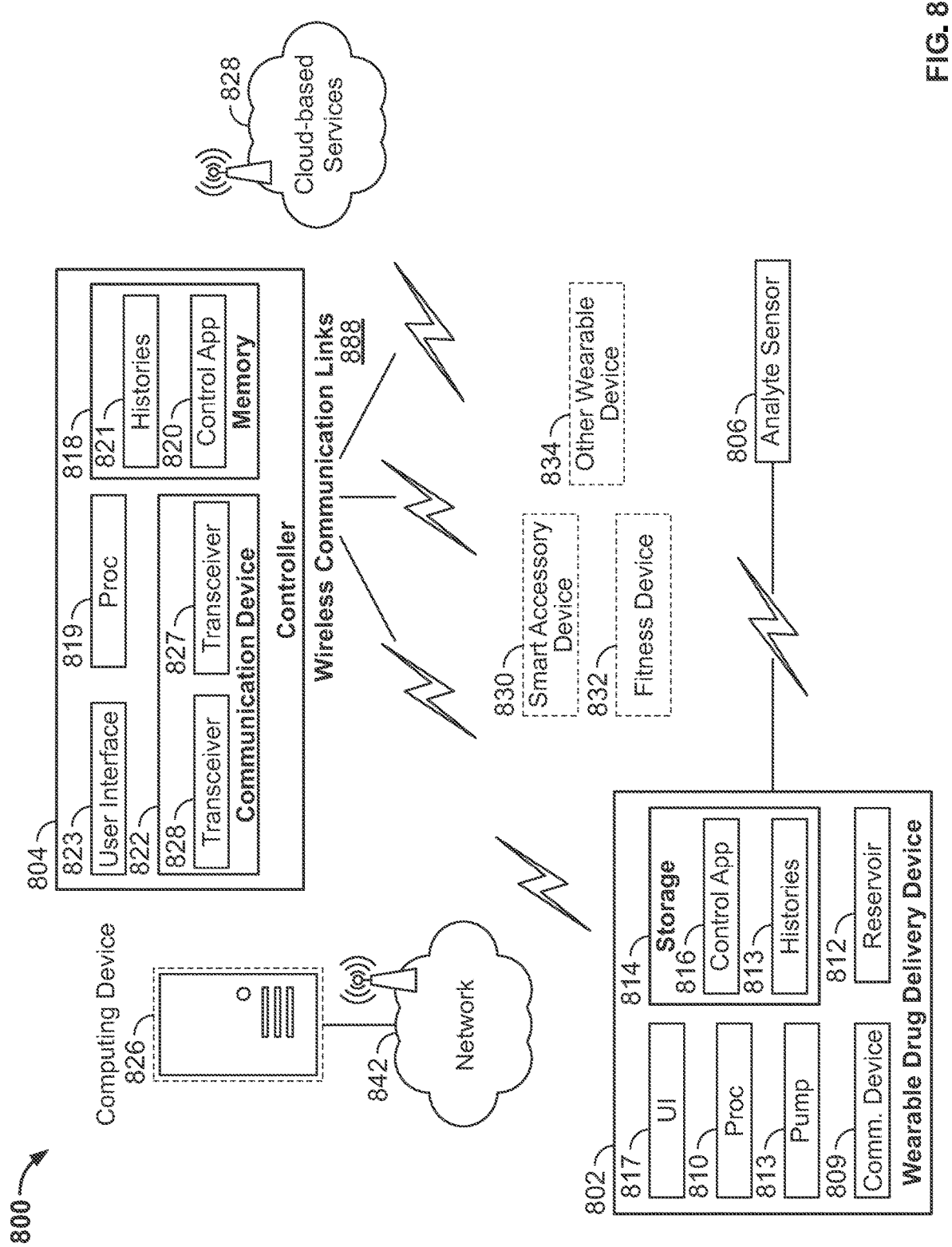
FIG. 8 illustrates a drug delivery system operable to implement the examples of FIGS. 1-7.

FIG. 8 illustrates a drug delivery system operable to implement the examples of FIGS. 1-7.

In some examples, the drug delivery system 800 that is suitable for delivering insulin to a user in accordance with exemplary embodiments. The drug delivery system 800 includes a wearable drug delivery device 802. The wearable drug delivery device 802 may be a wearable device that is worn on the body of the user. The wearable drug delivery device 802 may be directly coupled to a user (e.g., directly attached to a body part and/or skin of the user via an adhesive or the like). In an example, a surface of the wearable drug delivery device 802 may include an adhesive to facilitate attachment to the user.

The wearable drug delivery device 802 may include a processor 810. The processor 810 may be implemented in hardware, software, or any combination thereof. The processor 810 may, for example, be a microprocessor, a logic circuit, a field programmable gate array (FPGA), an application specific integrated circuit (ASIC) or a microprocessor coupled to a memory. The processor 810 may maintain a date and time as well as other functions (e.g., calculations or the like). The processor 810 may be operable to execute a control application 816 stored in the storage 814 that enables the processor 810 to direct operation of the wearable drug delivery device 802. The control application 816 may control insulin delivery to the user per an AID control approach as describe herein. The storage 814 may hold histories 815 for a user, such as a history of automated insulin deliveries, a history of bolus insulin deliveries, meal event history, exercise event history and the like. In addition, the processor 810 may be operable to receive data or information. The storage 814 may include both primary memory and secondary memory. The storage 814 may include random access memory (RAM), read only memory (ROM), optical storage, magnetic storage, removable storage media, solid state storage or the like.

The wearable drug delivery device 802 may include a reservoir 812. The reservoir 812 may be operable to store drugs, medications or therapeutic agents suitable for automated delivery, such as insulin, morphine, methadone, hormones, glucagon, glucagon-like peptide, blood pressure medicines, chemotherapy drugs, combinations of drugs, such as insulin and glucagon-like peptide, or the like. A fluid path to the user may be provided, and the wearable drug delivery device 802 may expel the insulin from the reservoir 812 to deliver the insulin to the user via the fluid path. The fluid path may, for example, include tubing coupling the wearable drug delivery device 802 to the user (e.g., via tubing coupling a cannula to the reservoir 812).

There may be one or more communications links with one or more devices physically separated from the wearable drug delivery device 802 including, for example, a controller 804 of the user and/or a caregiver of the user and/or a sensor 806. The communication links may include any wired or wireless communication link operating according to any known communications protocol or standard, such as Bluetooth®, Wi-Fi, a near-field communication standard, a cellular standard, or any other wireless protocol. The wearable drug delivery device 802 may also include a user interface 817, such as an integrated display device for displaying information to the user and in some embodiments, receiving information from the user. The user interface 817 may include a touchscreen and/or one or more input devices, such as buttons, knob or a keyboard.

The wearable drug delivery device 802 may interface with a network 842. The network 842 may include a local area network (LAN), a wide area network (WAN) or a combination therein. A computing device 826 may be interfaced with the network, and the computing device may communicate with the insulin delivery device 802. The computing device 826 may be a healthcare provider device through which the user may interact with the user's controller 804. The AID algorithm controlled via the control application 820 may present a graphical user interface on the computing device 826 similar to the graphic user interface 204 of FIG. 2 so a healthcare provider or guardian may input information, such as that described with reference to the earlier examples.

The drug delivery system 800 may include a sensor 806 for sensing the levels of one or more analytes. The sensor 806 may be coupled to the user by, for example, adhesive or the like and may provide information or data on one or more medical conditions and/or physical attributes of the user. The sensor 806 may be a continuous glucose monitor (CGM), or another type of device or sensor that provides blood glucose measurements that is operable to provide blood glucose concentration measurements. The sensor 806 may be physically separate from the wearable drug delivery device 802 or may be an integrated component thereof. The sensor 806 may provide the processor 810 with data indicative of measured or detected blood glucose levels of the user. The information or data provided by the sensor 806 may be used to adjust drug delivery operations of the wearable drug delivery device 802.

The drug delivery system 800 may also include the controller 804. In some embodiments, no controller is needed. The controller 804 may be a special purpose device, such as a dedicated personal diabetes manager (PDM) device. The controller 804 may be a programmed general-purpose device, such as any portable electronic device including, for example, a dedicated processor, such as processor, a micro-processor or the like. The controller 804 may be used to program or adjust operation of the wearable drug delivery device 802 and/or the sensor 806. The controller 804 may be any portable electronic device including, for example, a dedicated device, a smartphone, a smartwatch or a tablet. In the depicted example, the controller 804 may include a processor 819 and a memory/storage 818. The processor 119 may execute processes to manage a user's blood glucose levels and for control of the delivery of a drug or therapeutic agent to the user. The processor 819 may also be operable to execute programming code stored in the storage 818. For example, the storage may be operable to store one or more control applications 820, such as an AID algorithm for execution by the processor 819. The one or more control applications 820 may be responsible for controlling the wearable drug delivery device 802, including the automatic delivery of insulin based on recommendations and instructions provided by the AID algorithm to the user. For example, the AID algorithm as part of the one or more control applications 820 may generate a signal according to a determined dosage of insulin and cause the processor 819 to forward the signal via a transceiver, such as 828 or 827 of the communication device 822, to the wearable drug delivery device 802. The memory or storage 818 may store the one or more control applications 820, histories 821 like those described above for the insulin delivery device 802 and other data and/or programs.

The controller 804 may include a user interface (UI) 823 for communicating with the user. The user interface 823 may include a display, such as a touchscreen, for displaying information. The touchscreen may also be used to receive input when it is a touch screen. The user interface 823 may also include input elements, such as a keyboard, button, knob or the like.

The controller 804 may interface via a wireless communication link of the wireless communication links 888 with a network, such as a LAN or WAN or combination of such networks that provides one or more servers or cloud-based services 828. The cloud-based services 828 may be operable to store user history information, such as blood glucose measurement values over a set period of time (e.g., days, months, years), insulin delivery amounts (both basal and bolus dosages), insulin delivery times, types of insulin, indicated mealtimes, blood glucose measurement value trends or excursions or other user-related diabetes treatment information.

Other devices, like smart accessory device 830 (e.g., a smartwatch or the like), fitness device 832 and wearable device 834 may be part of the drug delivery system 800. These devices may communicate with the wearable drug delivery device 802 to receive information and/or issue commands to the wearable drug delivery device 802. These devices 830, 832 and 834 may execute computer programming instructions to perform some of the control functions otherwise performed by processor 810 or processor 819. These devices 830, 832 and 834 may include input/output devices, such as touchscreen displays for displaying information such as current blood glucose level, insulin on board, insulin deliver history, or other parameters or treatment-related information and/or receiving inputs, which may include signals containing the information from the analyte sensor 806. The display may, for example, be operable to present a graphical user interface for providing input, such as request a change in basal insulin dosage or delivery of a bolus of insulin. These devices 830, 832 and 834 may also have wireless communication connections with the sensor 806 to directly receive blood glucose level data.

In an operational example, the controller 804 includes a processor. The processor 819 of the controller 804 may execute an AID algorithm that is one of the control applications 820 stored in the memory or storage 818. The processor may be operable to present, on an input/output device that is the user interface 823, a graphical user interface that offers input fields for a generalized parameter of a number of generalized parameters of the AID algorithm. The number of generalized parameters is substantially less than a number of specific parameters of the AID algorithm. The processor 819 may receive an input of at least one generalized parameter corresponding to a user. In response to receiving the input of the at least one generalized parameter, the processor may set one or more of the number of specific parameters of the automated insulin delivery algorithm based on the inputted at least one generalized parameter. The processor 819 may begin collecting physiological condition data related to the user from sensors, such as the analyte sensor 806 or heart rate data from the fitness device 832 or smart accessory device 830. The processor 819 executing the AID algorithm may determine a dosage of insulin to be delivered based on the collected physiological condition of the user. The processor 819 may output a signal via one of the transceivers 827 or 828 to the wearable drug delivery device 802. The outputted signal may cause the pump 813 to deliver an amount of related to the determined dosage of insulin in the reservoir 812 to the user based on an output of the AID algorithm.

In another operational example, the controller 804 may be operable to execute programming code that causes the processor 819 of the controller 804 to perform the following functions. The processor 819 may in response to receipt of a user selected basal setting, determine value of an hourly basal insulin delivery factor. The value of the hourly basal insulin delivery factor may be reduced by a predetermined percentage to provide a minimized hourly basal insulin delivery factor. A maximum value between the reduced-percentage insulin delivery factor and a sum of a modified recommended basal dosage and a modified, user-selected basal dosage may also be determined. The processor 819 may determine a minimum between the determined maximum and a maximized hourly basal insulin delivery factor and may set a final basal dosage setting of the AID algorithm to the determined minimum. The AID algorithm may generate instructions for the pump 813 to deliver basal insulin to the user that remains below the determined minimum amount which is the final basal dosage setting for a period of time such as a day or the like.

In yet another operational example, the controller 804 may be operable to execute programming code that causes the processor 819 of the controller 804 to perform the following functions. The processor 819 may in response to receipt of a user selected correction factor setting, determine a value of a daily correction factor. The value of the daily correction factor may be reduced by a predetermined percentage to provide a minimized daily correction factor. A maximum value between the minimized daily correction factor and a sum of a modified recommended correction factor and a modified, user-selected correction factor may be determined. The processor 819 may determine a minimum between the determined maximum and a maximized daily correction factor. The processor 819 may set a final correction factor setting to the determined minimum. The AID algorithm may generate instructions for the pump 813 to deliver basal insulin to the user according to the final correction factor setting.

In a further operational example, the controller 804 may be operable to execute programming code that causes the processor 819 of the controller 804 to perform the following functions. The processor 819 may in response to receipt of a user selected insulin-to-carbohydrate setting, determine a value of a daily insulin-to-carbohydrate factor. The value of the daily insulin-to-carbohydrate factor may be reduced by a predetermined percentage to provide a minimized daily correction factor. A maximum value between the minimized daily insulin-to-carbohydrate factor and a sum of a modified recommended insulin-to-carbohydrate factor and a modified, user-selected insulin-to-carbohydrate factor may be determined by the processor 819. In addition, the processor 819 may determine a minimum between the determined maximum and a maximized daily insulin-to-carbohydrate factor. The processor 819 may set a final insulin-to-carbohydrate setting to the determined minimum. The AID algorithm may generate instructions for the pump 813 to deliver basal insulin to the user according to the final insulin-to-carbohydrate setting.

Further the insulin delivery recommendations provided by the AID algorithm may be individualized based on the user's response in the past. Glucose excursion patterns, incidences of hyperglycemia/hypoglycemia, and the like may be used to optimize insulin delivery for the future.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, novel subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible considering this disclosure. It is intended that the scope of the present disclosure be limited not by this detailed description, but rather by the claims appended hereto. Future filed applications claiming priority to this application may claim the disclosed subject matter in a different manner and may generally include any set of one or more features as variously disclosed or otherwise demonstrated herein.

What is claimed is:

1. A controller, comprising:
a processor;
an input/output device; and
a memory storing instructions that, when executed by the processor, configure the processor to:
present, on the input/output device, a graphical user interface offering a plurality of input fields that correspond to a plurality of generalized parameters of an automated insulin delivery algorithm, wherein at least one input field of the plurality of input fields presents a first reference value and a second reference value of a generalized parameter on the graphical user interface;
receive in the at least one input field via the input/output device an input of the generalized parameter between the first reference value and the second reference value;
in response to receiving the input of the generalized parameter, set a specific parameter of the automated insulin delivery algorithm based on the inputted generalized parameter;
determine, by the automated insulin delivery algorithm using the set specific parameter that was set based on the inputted generalized parameter, a dosage of insulin to be delivered to the user; and
cause the determined dosage of insulin to be delivered to the user.

2. The controller of claim 1, wherein the specific parameter includes an estimated initial total daily insulin (TDI) amount, an upper boundary of insulin delivery, a basal/bolus ratio, an insulin-on-board (IOB) amount, or a combination of two or more of the foregoing.

3. The controller of claim 1, wherein the inputted generalized parameter is a reference basal of the user.

4. The controller of claim 1, wherein the inputted generalized parameter is a user's weight and the processor, when setting the specific parameter of the automated insulin delivery algorithm based on the inputted sole generalized parameter, is operable to:
set an upper boundary for an amount of insulin to be delivered to the user.

5. The controller of claim 1, wherein the processor is further operable to:
generate a request for confirmation of a value of the set specific parameter by presenting a confirmation button in the graphical user interface on the input/output device;
allow the user to increase or decrease the value of the set specific parameter; and
receive an input confirming the value of the set specific parameter.

6. The controller of claim 1, wherein the processor is further operable to:
generate a signal according to the determined dosage of insulin; and
forward the signal to a wearable drug delivery device.

7. The controller of claim 1, wherein the processor is further operable to:
collect physiological condition data related to the user; and
modify the set specific parameter up or down over time to reflect an insulin need of the user.

8. A method, comprising:
presenting, on an input/output device of a user device, a graphical user interface offering a plurality of input fields that correspond to a plurality of generalized parameters of an automated insulin delivery algorithm, wherein at least one input field of the plurality of input fields of the graphical user interface presents a first reference value and a second reference value of a generalized parameter on the graphical user interface;
receiving in the at least one input field via the input/output device an input of the generalized parameter within the first reference value and the second reference value;
in response to receiving the input of the generalized parameter, setting a specific parameter of the automated insulin delivery algorithm based on the inputted generalized parameter;
determining, by the automated insulin delivery algorithm using the set specific parameter that was set based on the inputted generalized parameter, a dosage of insulin to be delivered to a user; and
causing the determined dosage of insulin to be delivered to the user.

9. The method of claim 8, wherein the number of specific parameters includes at least one of an estimated initial total daily insulin (TDI) amount, an upper boundary of insulin delivery, a basal/bolus ratio, and an insulin-on-board (IOB) amount.

10. The method of claim 8, wherein the inputted generalized parameter is a reference basal of the user.

11. The method of claim 10, wherein the method further comprises:
setting an upper boundary an amount of insulin to be delivered to the user.

12. The method of claim 8, wherein the method further comprises:
generating a request for confirmation of a value of the set specific parameter by presenting a confirmation button in the graphical user interface on the input/output device;
presenting an option to allow the user to modify the value of the set specific parameter; and
receiving an input confirming the value, whether modified or not, of the set specific parameter.

13. The method of claim 8, wherein causing the determined dosage of insulin to be delivered to the user, further comprises:
generating a signal according to the determined dosage of insulin; and
forwarding the signal to a wearable drug delivery device.

14. A system comprising:
a non-transitory computer-readable storage medium, the computer-readable storage medium including instructions that when executed by at least one processor, cause the at least one processor to:
present, on an input/output device, a graphical user interface offering a plurality of input fields that correspond to a plurality of generalized parameters of an automated insulin delivery algorithm, wherein at least one input field of the plurality of input fields presents a first reference value and a second reference value of a generalized parameter on the graphical user interface;
receive in the at least one input field via the input/output device via the input/output device an input of only one generalized parameter between the first reference value and the second reference value presented on the graphical user interface;
in response to receiving the input of the only one generalized parameter, set a specific parameter of the automated insulin delivery algorithm based on the only one inputted generalized parameter;
determine, by the automated insulin delivery algorithm using the set specific parameter that was set based on the only one inputted generalized parameter, a dosage of insulin to be delivered to the user; and
cause the determined dosage of insulin to be delivered to the user.

15. The system of claim 14, wherein the specific parameter includes an estimated initial total daily insulin (TDI) amount, an upper boundary of insulin delivery, a basal/bolus ratio, an insulin-on-board (IOB) amount, or a combination of two or more of the foregoing.

16. The system of claim 14, wherein the only one inputted generalized parameter is a reference of the user.

17. The system of claim 16, wherein the instructions further cause the at least one processor, when setting the specific parameter of the automated insulin delivery algorithm based on the inputted only one generalized parameter, to:
set an upper boundary for an amount of insulin to be delivered to the user.

18. The system of claim 14, wherein the instructions further cause the at least one processor to:
generate a request for confirmation of a value of the set specific parameter by presenting a confirmation button in the graphical user interface on the input/output device;
allow the user to increase or decrease the value of the set specific parameter; and
receive an input confirming the value of the set specific parameter.

19. The system of claim 14, further comprising:
a wearable drug delivery device having a processor executing the automated insulin delivery algorithm, and the processor of the wearable drug delivery device is operable to:
  perform the determining of the dosage of insulin to be delivered to the user using the set specific parameter.

20. The system of claim 14, wherein the instructions further cause the processor to:
collect physiological condition data related to the user; and
modify the set specific parameter up or down to reflect an insulin need of the user indicated by the collected physiological condition data.

* * * * *